(12) United States Patent
Yuspa et al.

(10) Patent No.: US 7,056,908 B2
(45) Date of Patent: Jun. 6, 2006

(54) PHARMACEUTICAL COMPOSITIONS AND METHODS FOR PREVENTING SKIN TUMOR FORMATION AND CAUSING REGRESSION OF EXISTING TUMORS

(75) Inventors: Stuart H. Yuspa, Bethesda, MD (US); Andrzej Dlugosz, Rockville, MD (US); Henry Hennings, Gaithersburg, MD (US); James Strickland, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 372 days.

(21) Appl. No.: 10/445,251

(22) Filed: May 27, 2003

(65) Prior Publication Data

US 2004/0048845 A1    Mar. 11, 2004

Related U.S. Application Data

(60) Division of application No. 08/876,510, filed on Jun. 16, 1997, now abandoned, which is a continuation of application No. 07/677,429, filed on Mar. 29, 1991, now abandoned.

(51) Int. Cl.
    *A61K 31/553*    (2006.01)

(52) U.S. Cl. .................................................. 514/211.08
(58) Field of Classification Search ............ 514/211.08
    See application file for complete search history.

(56) References Cited

OTHER PUBLICATIONS

Kiyoto, Itsumi, Inhibition of tumor promotion by staurosporine, a potent protein kinase C inhibitor., Keio Igaku, (abstract only) 1989, vol. 66(1), pp. 69-88.*
Watanabe et al., Dual effects of staurosporine of arachidonic acid metabolism . . . (abstract only) Biochimica et Biophysica Acta, (1990), vol. 1047(2), pp. 141-147.*
Yoshizawa et al., Tumor-promoting activity of staurosporine . . . , (abstract only), Cancer Research (1991) vol. 50(16), pp. 4974-4978.*
Yamamoto et al., Differential inhibition by staurosporine, a potent protein kinase C inhibitor, . . . (abstract only) Carcinogenesis (1989), vol. 10(7), pp. 1315-1322.*

* cited by examiner

*Primary Examiner*—Vickie Kim
(74) *Attorney, Agent, or Firm*—Venable.LLP; Thomas G. Wiseman

(57) ABSTRACT

Pharmaceutical compositions and methods for treating epithelial cancers and precancerous lesions employ indole carbazole compounds, such as staurosporine. Compositions containing these compounds are administered to a patient in an effective amount and may be administered topically.

8 Claims, 13 Drawing Sheets

PHARMACEUTICAL COMPOSITIONS AND METHODS FOR PREVENTING SKIN TUMOR FORMATION AND CAUSING REGRESSION OF EXISTING TUMORS

This application is a divisional application of Ser. No. 08/876,510 filed Jun. 16, 1997 now abandoned, which is a continuation application of Ser. No. 07/677,429 filed Mar. 29, 1991 now abandoned.

BACKGROUND OF THE INVENTION

1. Field of the Invention

The present invention relates to pharmaceutical compositions and methods for preventing skin tumor formation and causing regression of existing skin tumors. More specifically, the present invention relates to methods for treating precancerous lesions and skin cancer which include administering to a patient an effective amount of indole carbazole compounds as well as to pharmaceutical compositions containing indole carbazole compositions and a pharmaceutically acceptable excipient.

2. Description of Related Art

Previous approaches to prevent or treat epithelial cancers have relied on two strategies. In one, toxic drugs are used which generally interfere with DNA synthesis directly and kill both normal and tumorous cells. The mode of killing is by a direct cytotoxic mechanism. A second technology which has been in use previously is the prevention of tumors by treatment with retinoids, analogs of Vitamin-A. The mechanism of action of retinoids is not understood, but the influence appears to be suppressive rather than curative. There is no induction of the normal terminal differentiation pathways and upon withdrawal of the retinoids, tumors return. Therefore, it is desired to discover methods for treating epithelial cancers as well as precancerous lesions which utilizes a normal physiologic pathway so as to target tumorous cells. It is further desired to discover treatments which cause terminal differentiation of tumor cells so as to have a curative rather than merely suppressive effect.

The mouse skin carcinogenesis model has provided insights into both early events in the development of epithelial neoplasia as well as later changes associated with neoplastic progression. The ability to cultivate keratinocytes in vitro has further facilitated analysis of both genetic and epigenetic events that are important in cutaneous neoplasia. For example, the tumor promoter TPA[3] is a potent inducer of maturation in cultured primary mouse keratinocytes but not neoplastic cells. This differential response in vitro may provide insight into the mechanism by which phorbol esters promote tumor formation in vivo. Repeated application of TPA to initiated mouse skin is associated with accelerated maturation and desquamation of normal keratinocytes which permits the clonal expansion of differentiation-resistant initiated cells into a papilloma. An important corollary to this observation is that restoring the ability of neoplastic keratinocytes to differentiate would render them non-tumorigenic.

PKC is composed of a family of phospholipid-dependent kinases which phosphorylate proteins at serine and threonine residues. Since phorbol esters bind and activate PKC, this enzyme has been implicated in TPA-mediated responses such as the induction of differentiation markers in primary keratinocytes. Several classes of inhibitors have been used in an attempt to better understand the functions of PKC; unfortunately, all of these also inhibit other protein kinases which complicates the interpretation of results using intact cells. One of the most potent inhibitors presently available is staurosporine (Tamaoki, T. et al, "Staurosporine, a potent inhibitor of phospholipid/Ca++dependent protein kinase," *Biochem. Biophys. Res. Commun.*, 135: 397–402, 1986), which inhibits PKC at nanomolar doses in vitro by interacting with its catalytic domain (Nakadate, T. et al, "Comparison of protein kinase C functional assays to clarify mechanisms of inhibitor action," *Biochem. Pharmacol.*, 37: 1541–1545, 1988; and Gross, J. L. et al, "Characterization of specific [3H]dimethylstaurosporine binding to protein kinase C," *Biochem. Pharmacol.*, 40: 343–350, 1990). Whereas staurosporine blocks the effects of TPA in several non-epithelial cell types (Sako, T. et al, "Contrasting actions of staurosporine, a protein kinase C inhibitor, on human neutrophils and primary mouse epidermal cells," *Cancer Res.*, 48: 4646–4650, 1988; Ederveen, A. G. H. et al, "Dissimilar effects of the protein kinase C inhibitors, staurosporine and H-7, on cholecystokinin-induced enzyme secretion from rabbit pancreatic acini," *Eur. J. Biochem.*, 193: 291–295, 1990: Vegesna, R. V. et al, "Staurosporine inhibits protein kinase C and prevents phorbol ester-mediated leukotriene D4 receptor desensitization in RBL-1 cells," *Mol. Pharmacol.*, 33: 537–542, 1988; and Watson, S. P. et al, "The action of the protein kinase C inhibitor, staurosporine, on human platelets. Evidence against a regulatory role for protein kinase C in the formation of inositol triphosphate by thrombin," *Biochem. J.*, 249: 345–50, 1988), it fails to inhibit TPA-mediated maturation in primary mouse keratinocytes and induces certain responses characteristic of TPA exposure (Sako T. et al, "Contrasting actions of staurosporine, a protein kinase C inhibitor, on human neutrophils and primary mouse epidermal cells," *Cancer Res.*, 48: 4646–4650, 1988).

Previously, it has been reported that systemic administration of staurosporine to mice which were injected with human bladder carcinoma cells, could retard tumor growth by approximately 60% at ⅒ or ½₀ the maximum tolerated dose. Meyer et al, "A derivative of staurosporine (CGP 41 251) shows selectivity for protein kinase C inhibition and in vitro anti-proliferative as well as in vivo anti-tumor activity," *Int. J. Cancer*, 43, (1989), pp. 851–856). Using a cell culture assay, Schwartz et al ("Inhibition of Invasion of Invasive Human Bladder Carcinoma Cells . . . ," *J. of the Nat. Cancer. Inst.*, Vol. 82, No. 22, Nov. 21, 1990, pp. 1753–1756) suggested that staurosporine might inhibit tumor cell invasion of bladder cancer cells but this was not confirmed in vivo. Obrian et al ("Staurosporine: A Prototype of a Novel Class of Inhibitors of Tumor Cell Invasion?," Editorial, *J. of the Nat. Cancer Inst.*, Vol. 82, No. 22, Nov. 21, 1990, pp. 1734–1735) state that staurosporine may have antitumor activity because of its ability to inhibit protein kinases. Meyer et al, Schwartz et al and Obrian et al all fail to disclose the use of the staurosporine in treating cancerous or precancerous conditions of the skin.

In view of the above, it is desired to obtain a method for treating precancerous and cancerous conditions of the skin which is both effective and curative.

SUMMARY OF THE INVENTION

Therefore, it is an object of the present invention to provide methods for preventing and treating precancerous and cancerous conditions of the skin which overcome the above-noted problems.

It is another object of the present invention to provide pharmaceutical compositions and methods for causing regression of existing skin neoplastic lesions.

It is a further object of the present invention to provide methods of treating epithelial cancers as well as precancerous lesions which utilizes a normal physiologic pathway so as to target tumorous cells.

It is a still a further object of the present invention to provide methods of treating epithelial cancers as well as precancerous lesions which causes terminal differentiation of tumor cells thereby resulting in a curative effect.

It is yet a further object of the present invention to provide a method of topical application of staurosporine and potentially other indole carbazole compounds which can prevent skin tumor formation and induce terminal differentiation in skin tumor cells, thus causing a permanent eradication of the tumor mass.

The foregoing objects and others are accomplished in accordance with the present invention by providing methods for treating precancerous and cancerous conditions of the skin which include administering to a patient an effective amount of a composition containing indole carbazole compounds and a pharmaceutically acceptable excipient. In another embodiment of the methods of the present invention, precancerous and cancerous conditions of the skin are treated by administering topically to the skin of a patient a composition which contains indole carbazole compounds and a pharmaceutically acceptable excipient.

In another embodiment of the present invention, a pharmaceutical composition is provided which contains a pharmaceutically acceptable topical carrier in combination with indole carbazole compounds of the following formulas:

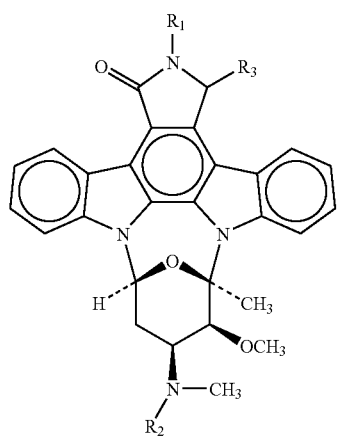

Formula 1 wherein $R_1$ is hydrogen or benzyl; $R_2$ is hydrogen or benzoyl; and $R_3$ is hydrogen or hydroxy.

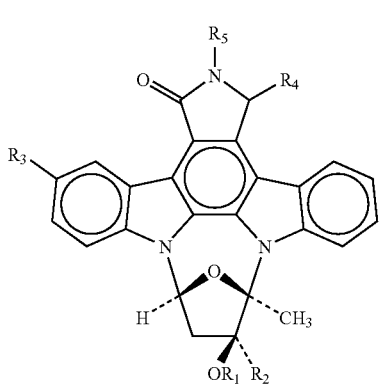

Formula 2 wherein $R_1$ is hydrogen or lower alkyl; $R_2$ is carboxyl or carboxylate esterified with a lower alkyl; $R_3$ is a hydrogen or lower alkoxy; and $R_4$ and $R_5$ are hydrogen.

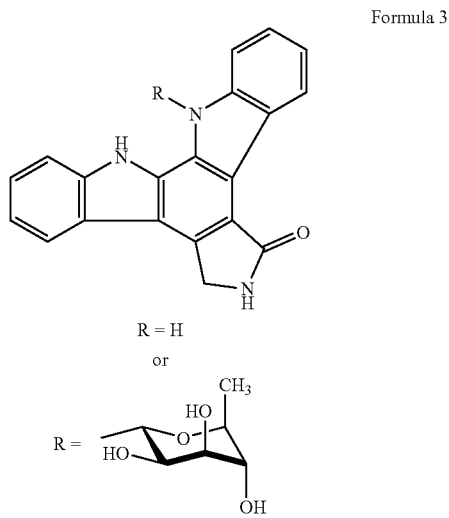

Formula 3

R = H or

R = [sugar structure]

Further scope of the applicability of the present invention will become apparent from the detailed description and drawings provided below. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The invention is further illustrated in the accompanying figures wherein.

DETAILED DESCRIPTION OF THE INVENTION

Figure 1:
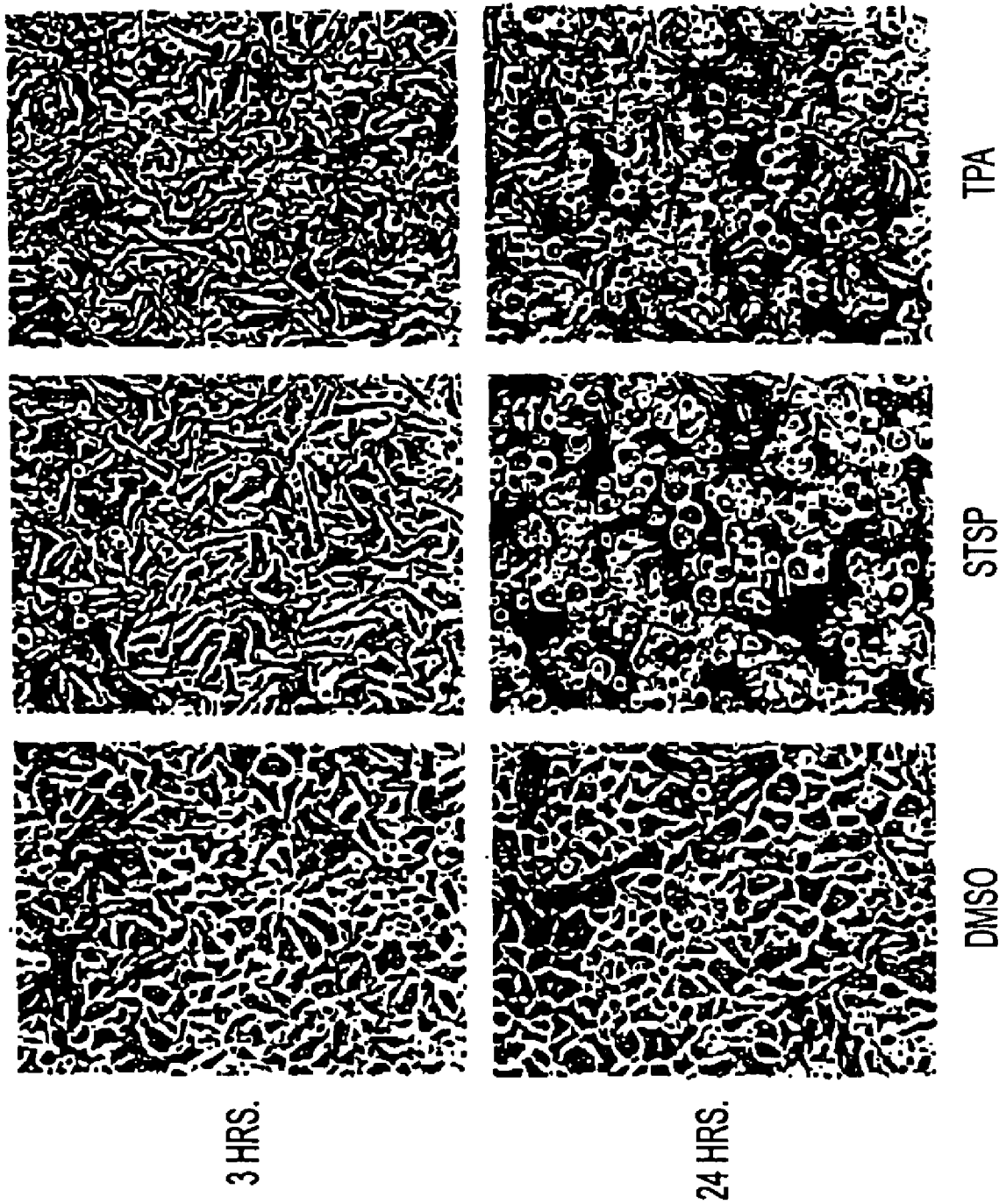
FIG. 1 shows phase-contrast photomicrographs (magnification×90) of staurosporine and TPA induced morphological changes in primary keratinocytes.

A purpose of the present invention is to prevent the formation of epithelial skin tumors, and other epithelial derived tumors which may be sensitive to similar exposures, by the induction of the normal state of terminal differentiation. An early change in the neoplastic process is resistance of signals which normally induce terminal differentiation in the parental tissue cells. Thus, tumor cells grow under conditions where normal cells of that tissue will terminally differentiate. In neoplastic skin cells in culture and in vivo, staurosporine and indole carbazole compounds of the present invention have the potential capacity to induce differentiation and to prevent tumor formation, respectively. The indole carbazole compounds of the present invention appear to work by usurping a normal physiologic pathway which is altered in neoplastic cells, i.e. the staurosporine and possibly other indole carbazole compounds may reverse this alteration to cause the normal program of differentiation to proceed. Thus, terminal differentiation is caused which apparently rids the treated organism of tumor cells resulting in a curative rather than suppressive effect.

The present inventors have discovered staurosporine and potentially other indole carbazole compounds, especially at certain doses, can cause changes generally attributed to activation of protein kinase C. Phorbol esters activate protein kinase C in normal skin cells but are ineffective in skin tumor cells. However, staurosporine causes the normal phorbol ester-like effects in skin tumor cells at appropriate doses. Staurosporine causes skin tumor cells in culture to terminally differentiate, stimulating the enzyme transglutaminase, causing cross-linking of the cell envelope and cell death. This action of staurosporine and indole carbazole compounds is irreversible and works on several kinds of benign and malignant skin tumor cells. When benign tumor cells are grafted to the skin of mice, they form tumors within several weeks. However, treatment of the graft sites with staurosporine completely prevents tumor formation in an irreversible manner. While indole carbazole compounds including staurosporine for topical treatment of precancerous and cancerous conditions of the skin are encompassed by the present invention, systemic administration of these compounds may also influence tumor growth in skin or act as a cancer prevention treatment. Other epithelial target sites, such as the colon, bladder and lung may also be influenced by treatment employing these compounds according to the present invention, since protein kinase C also regulates differentiation in the cells.

The indole carbazole compounds useful in the methods and pharmaceutical compositions of the present invention include those of the following formulas:

Formula 1

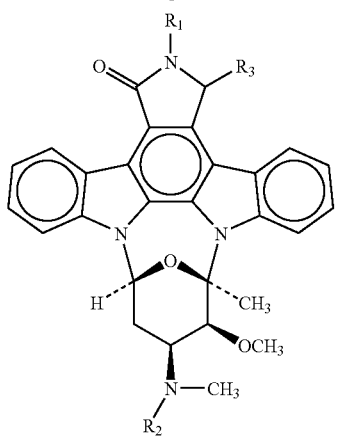

wherein $R_1$ is hydrogen or benzyl; $R_2$ is hydrogen or benzoyl; and $R_3$ is hydrogen or hydroxy.

Formula 2

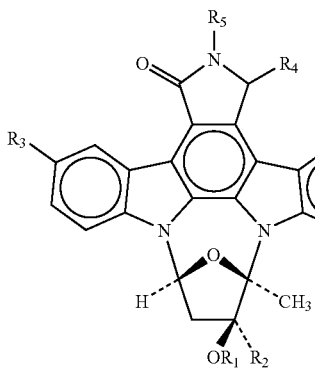

wherein $R_1$ is hydrogen or lower alkyl; $R_2$ is carboxyl or carboxylate esterified with a lower alkyl; $R_3$ is a hydrogen or lower alkoxy; and $R_4$ and $R_5$ are hydrogen.

Preferred compounds include those listed below in Tables 1, 2 and 3.

TABLE 1

| COMPOUND | $R_1$ | $R_2$ | $R_3$ |
| --- | --- | --- | --- |
| 1 | H | H | H |
| 2 | H | benzoyl | H |
| 3 | benzyl | benzoyl | H |
| 4 | H | H | OH |

Formula 1

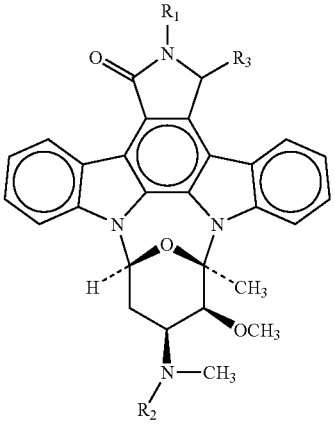

TABLE 2

| COMPOUND | $R_1$ | $R_2$ | $R_3$ | $R_4$ | $R_5$ |
| --- | --- | --- | --- | --- | --- |
| 5 | H | COOCH$_3$ | H | H | H |
| 6 | H | COOH | H | H | H |
| 7 | H | COOCH$_3$ | OCH$_2$CH$_2$CH$_3$ | H | H |
| 8 | H | COO(CH$_2$)$_5$CH$_3$ | H | H | H |
| 9 | CH$_3$ | COOCH$_3$ | H | H | H |

TABLE 2-continued

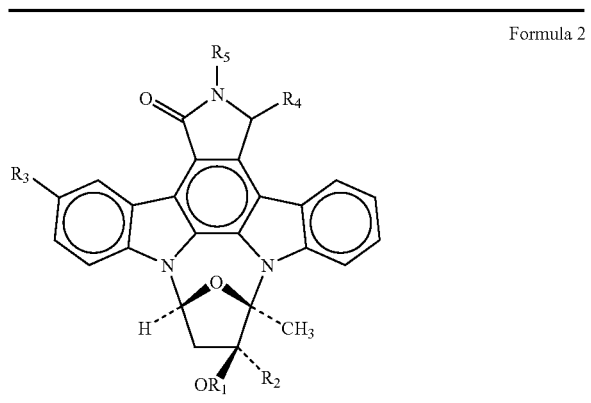

Formula 2

TABLE 3

| COMPOUND | R |
|---|---|
| 10 | H |
| 11 | (sugar group with $CH_3$, HO, HO, OH) |

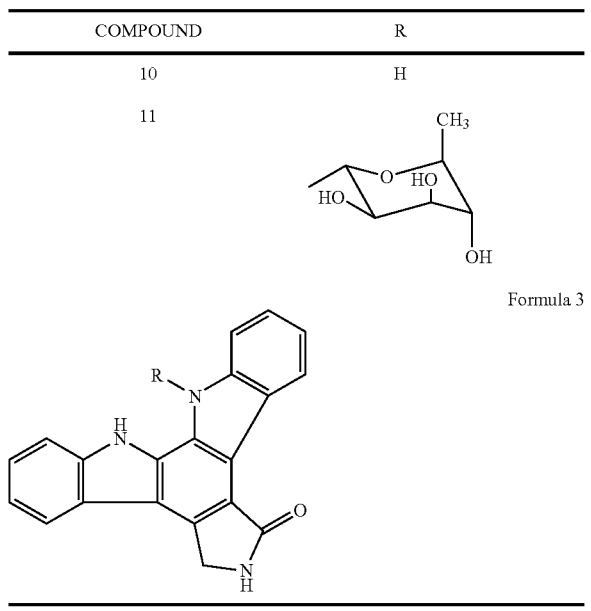

Formula 3

An especially preferred compound is staurosporine.

The indole carbazole compounds listed in Tables 1 and 2 encompassed by Formula 3 are all compounds known in the art. Compound 1 is staurosporine and is described in Takahashi et al, "UCN-01, a selective inhibitor of protein kinase C from streptomyces," *J. Antibiotics*, 40: 1782–1784, 1987. Compounds 2 and 3 are described in Meyer et al, "A derivative of staurosporine (CGP 41 251) shows selectively for protein kinase C inhibition and in vitro anti-proliferative as well as in vivo anti-tumor activity," *Int. J. Cancer*, 43: 851–856, 1989. Compound 4 is described in Takahashi et al, "Potent selective inhibition of 7-0-methyl UCN-01 against protein kinase C," *J. Pharmacol. Exp. Ther.*, 255: 1218–1221, 1990. Compound 5 is described in Kase et al, "K-252a, a potent inhibitor of protein kinase C from microbial origin," *J. Antibiotics*, 39: 1059–1065, 1986; and in Yasuzawa et al, "The structures of the novel protein kinase C inhibitors K-252a, b, c, and d," *J. Antibiotics*, 39: 1072–1078, 1986. Compounds 6, 10 and 11 are described in Yasuzawa et al, "The structures of the novel protein kinase C inhibitors K-252a, b, c, and d," *J. Antibiotics*, 39: 1072–1078, 1986; and in Nakanishi et al, "K-252b, c and d, potent inhibitors of protein kinase C from microbial origin," *J. Antibiotics*, 39: 1066–1071, 1986. Compound 7 is described in Nakanishi et al, "KT5926, a potent and selective inhibitor of myosin light chain kinase," *Mol. Pharmacol.*, 33: 482–488, 1990. Compounds 8 and 9 are described in Kase et al, "K-252 compounds, novel and potent inhibitors of protein kinase C and cyclic nucleotide-dependent protein kinases," *Biochem. Biophys. Res. Commun.*, 142: 436–440, 1987.

The indole carbazole compounds employed in the present invention are used for treating a variety of precancerous lesions and skin cancers including keratoacanthoma, actinic keratosis, basal cell carcinoma, squamous cell carcinoma, Bowen's disease and verrucae. A first embodiment of a method of treatment in accordance with the present invention includes administering to a patient an effective amount of a pharmaceutical composition containing indole carbazole compounds and a pharmaceutically acceptable excipient in order to treat epithelial cancers and/or precancerous lesions.

In a second embodiment of the present invention, a method is provided wherein precancerous and cancerous conditions of the skin are treated by administering topically to the skin of a patient a pharmaceutical composition which contains indole carbazole compounds and a pharmaceutically acceptable excipient. Topical treatment allows application of the active agent directly and selectively to the involved lesions and thus minimizes possible toxicity to noninvolved sites.

The pharmaceutical composition encompassed by the present invention contains the above-noted indole carbazole compounds along with a pharmaceutically acceptable excipient, such as a topical carrier.

The indole carbazole compounds employed in the present invention may be made into pharmaceutical compositions by combination with appropriate pharmaceutically acceptable carriers or diluents, and may be formulated into preparations in solid, semi-solid, liquid or gaseous forms such as tablets, capsules, powders, granules, ointments, creams, lotions, solutions, suppositories, injections, inhalants, and aerosols in the usual ways for their respective route of administration. The following methods and excipients are merely exemplary and are in no way limiting.

In pharmaceutical dosage forms, the indole carbazole compounds employed in the present invention may be used in the form of their pharmaceutically acceptable salts, and also may be used alone or in appropriate association, as well as in combination with other pharmaceutically active compounds.

In the case of oral preparations, the indole carbazole compounds may be used alone or in combination with appropriate additives to make tablets, powders, granules or capsules, e.g. with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc magnesium stearate; and if desired, with diluents, buffering agents, moistening agents, preservatives and flavoring agents.

Furthermore, the indole carbazole compounds employed in the present invention may be made into suppositories by mixing with a variety of bases such as emulsifying bases or water-soluble bases.

The indole carbazole compounds employed in the present invention may be formulated into preparations for injections by dissolving, suspending or emulsifying them in an aqueous or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In the cases of inhalations or aerosol preparations, the indole carbazole compounds employed in the invention in the form of a liquid or minute powder may be filled up in an aerosol container with gas or liquid spraying agents, and if desired, together with conventional adjuvants such as humidifying agents. They may also be formulated as pharmaceuticals for non-pressured preparations such as in a nebulizer or an atomizer.

The amount staurosporine or the indole carbazole compounds employed in the present invention to be used varies according to the degree of the pathology encountered and the stage of the disease. A suitable topical dosage is 6.25–0.00625 nmole/cm$^2$ applied topically to the targeted precancerous or cancerous cells and is more preferably 0.625–0.00625 nmole/cm$^2$. This dosage may be affected by route of administration, solvent, toxicity or pain.

Unit dosage forms for oral administration such as syrups, elixirs, and suspensions wherein each dosage unit, e.g., teaspoonful, tablespoonful, contains a predetermined amount of the indole carbazole compounds employed in the present invention can be by a pharmaceutically acceptable carrier, such as Sterile Water for Injection, USP, or by normal saline.

The indole carbazole compounds employed in the present invention can be administered rectally via a suppository. The suppository can include vehicles such as cocoa butter, carbowaxes and polyethylene glycols, which melt at body temperature, yet are solidified at room temperature.

The indole carbazole compounds employed in the present invention can be utilized in aerosol formulation to be administered via inhalation. The indole carbazole compounds employed in the present invention can be formulated into pressurized acceptable propellants such as dichlorodifluoromethane, propane, nitrogen and the like.

The term "unit dosage form" as used herein refers to physically discrete units suitable as unitary dosages for human and animal subjects, each unit containing a predetermined quantity of the indole carbazole compounds calculated in an amount sufficient to produce the desired effect in association with a pharmaceutically acceptable, diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, for example, vehicles, adjuvants, carriers or diluents are readily available to the public.

Any necessary adjustments in dose can be readily made to meet the severity of the pathology and adjusted accordingly by the skilled practitioner.

Inducement by Staurosporine of Protein Kinase C Agonist Effects and Maturation of Normal and Neoplastic Mouse Keratinocytes In Vitro

MATERIALS AND METHODS

Materials. Staurosporine was purchased from Calbiochem, La Jolla, Calif.; TPA from LC Services, Woburn, Mass.; $^3$H-putrescine, $^{14}$C-ornithine, $^{125}$I-EGF, and $\gamma^{32}$P-ATP from NEN, Boston, Mass.; EGF (receptor grade) from Collaborative Research, Bedford, Mass.; and digitonin (~50% powder) from Sigma, St. Louis, Mo. Bryostatin (bryostatin 1) was generously provided by Dr. G. R. Pettit, Arizona State University, Tempe, Ariz.

Cell Culture. Primary epidermal keratinocytes were isolated from newborn Balb/c mice as described (Hennings, H. et al, "Calcium regulation of growth and differentiation of mouse epidermal cells in culture," Cell, 19: 245–254, 1980). The neoplastic keratinocyte cell line 308 was established from Balb/c mouse skin initiated with 7,12-dimethylbenz[a] anthrax-cene in vivo, the SP-1 cell line from papillomas produced on Sencar mice by initiation with 7, 12-dimethylbenz[a] anthracene and 12-0-tetradecancylphorbol (TPA) promotion (Strickland, J. E, et al, "Development of murine epidermal cell lines which contain an activated rasHa oncogene and form papillomas in skin grafts on athymic nude mouse hosts," Cancer Res., 48: 165–169, 1988). Both 308 and SP-1 cells form benign papillomas when grafted onto the backs of immune-deficient mice (Strickland, J. E, et al, "Development of murine epidermal cell lines which contain an activated rasHa oncogene and form papillomas in skin grafts on athymic nude mouse hosts," Cancer Res., 48: 165–169, 1988). Primary as well as neoplastic keratinocytes were cultured in Eagle's minimum essential medium containing 8% chelexed fetal calf serum and 1% antibiotic/antimycotic solution (Hennings, H. et al, "Calcium regulation of growth and differentiation of mouse epidermal cells in culture," Cell, 19: 245–254, 1980). Unless otherwise indicated, the concentration of Ca$^{2+}$ in the medium was adjusted to 0.05 mM to maintain a basal cell-like population of undifferentiated cells (Yuspa, S. H. et al, "Expression of murine epidermal differentiation markers is tightly regulated by restricted extracellular calcium concentrations in vitro," J. Cell Biol., 109: 1207–1217, 1989).

Enzyme Assays. Activity of epidermal transglutaminase was determined by measuring cross-linking of $^3$H-putrescine to dimethylcasein (20). Cell lysates were incubated at 37° for 10 minutes to inactivate tissue transglutaminase. Ornithine decarboxylase activity of cell lysates was determined by quantifying release of $^{14}$CO$_2$ from $^{14}$C-ornithine (Sako, T. et al, "Partial parallelism and partial blockade by bryostatin 1 of effects of phorbol ester tumor promoters on primary mouse epidermal cells," Cancer Res., 47: 5445–5450, 1987).

Cornified Envelope Quantitation. Keratinocytes were analyzed for cornified envelope formation as described (Nagae, S. et al, "Effect of retinoic acid on cornified envelope formation: difference between spontaneous envelope formation in vivo or in vitro and expression of envelope competence," J. Invest., Dermatol., 89: 51–58, 1987), with minor modifications. Floating cells were harvested by collecting culture medium from each 60 mm dish and combining with two washes using phosphate-buffered saline without Ca$^{2+}$ and Ms$^{+2}$ (PBS). Cells were pelleted for 5 minutes at 1000 rpm in a benchtop clinical centrifuge and resuspended in 100 µl of lysis buffer (2% sodium dodecyl sulfate (SDS) and 20 mM dithiothreitol in PBS). Attached cells were harvested in 250 µl lysis buffer, combined with the preparation of floating cells, and incubated at 95° for 10 minutes. The non-solubilized, intact cornified envelopes, characteristic of terminally differentiated keratinocytes, were counted using a hemocytometer (Nagae, S. et al, "Effect of retinoic acid on cornified envelope formation: difference between spontaneous envelope formation in vivo or in vitro and expression of envelope competence," J. Invest. Dermatol., 89: 51–58, 1987).

$^{125}$I-Epidermal Growth Factor (EGF) Binding. EGF binding was assessed in 6-well tissue culture dishes plated at a cell density of 2.5×10⁶ cells/well (Strickland, J. E. et al, "Interaction of epidermal growth factor with basal and differentiating epidermal cells of mice resistant and sensitive to carcinogenesis," *Carcinogenesis*, 5: 735–740, 1984). After treatment, cultures were washed twice with binding buffer (Dulbecco's minimum essential medium with 50 mM N,N-bis-(2-hydroxyethyl)-2-aminosulfonic acid (pH 6.8) and 1 mg/ml bovine serum albumin) at 4°, then incubated with 1 ml binding buffer containing $_{125}$I-EGF (1.4×10⁵ dpm) for 4–6 hours on a bed of ice (Strickland, J. E. et al, "Interaction of epidermal growth factor with basal and differentiating epidermal cells of mice resistant and sensitive to carcinogenesis," *Carcinogenesis*, 5: 735–740, 1984). A second set of cultures received, in addition, 1 µg/ml unlabelled EGF to assess non-specific binding of radioactive ligand. Following the incubation period, cultures were washed 4 times with ice-cold binding buffer, harvested in 1.5 ml lysis buffer (0.1 M tris (pH 7.4), 0.5% SDS, 1 mM EDTA), and radioactivity determined by scintillation counting.

RNA Isolation and Northern Blot Analysis. RNA was isolated by ultracentrifugation of guanidine isothiocyanate lysates through a 5.7M cesium chloride gradient (Chirgwin, J. M. et al, "Isolation of biologically active ribonucleic acid from sources enriched in ribonuclease," *Biochemistry*, 18: 5294–5299, 1979). 20 µg of total RNA was loaded per lane and electrophoresed through a 1% agarose gel containing 0.66 M formaldehyde (Davis, L. G. et al, "Basic Methods in Molecular Biology," New York: Elsevier, 1986). RNA was blotted to reinforced nitrocellulose membrane (BA-S NC; Schleicher & Schuell, Keene, N.H.) and baked at 80° C. in a vacuum oven for 2 hours. Filter were pre-hybridized at 42° overnight in buffer containing 50% formamide as previously described (Yuspa, S. H. et al, "Expression of murine epidermal differentiation markers is tightly regulated by restricted extracellular calcium concentrations in vitro," *J. Cell Biol.*, 109: 1207–1217, 1989); approximately 20×10⁶ dpm of probe was added and hybridization carried out overnight. The final wash performed at 65° using 0.2×SSC with 0.1% SDS. Filters were exposed to Kodak X-Omat AR film at −70° with intensifying screens. Mouse c-fos transcript was detected using a 1.2 kb Bgl II to Sal I fragment from the Finkel-Biskis-Jinkins murine sarcoma virus sequence (Curran, T. et al, "Structure of the FBJ murine osteosarcoma virus genome: molecular cloning of the associated helper virus and the cellular homologue of the v-fos gene from mouse and human cells," *Mol. Cell. Biol.*, 3: 914–921, 1983). Following autoradiography, remaining probe was removed by washing in 1% glycerol in deionized water at 80° for 2 minutes (Davis, L. G. et al, "Basic Methods in Molecular Biology," New York: Elsevier, 1986) and the filter was re-hybridized to a full-length rat glyceraldehyde phosphate dehydrogenase (GAPDH) cDNA in a pUC18 vector (Fort, P. et al, "Various rat adult tissues express only one major mRNA species from the glyceraldehydes-3-phosphate-dehydrogenase multigenic family," *Nucleic. Acids. Res.*, 13: 1431–1442, 1985). Probes were labelled by random priming to a specific activity of 5×10⁸ cpm/µg DNA.

Cell Permeabilization and $^{32}$P-Labelled Phosphoprotein Analysis. Primary mouse keratinocytes were permeabilized with digitonin to facilitate uptake of $^{32}$P-ATP essentially as described (Erusalimsky, J. D. et al, "Diacylglycerols, and phorbol esters rapidly stimulate the phosphorylation of an Mr=80,000 protein kinase C substrate in permeabilized 3T3 cells," *J. Biol. Chem.*, 263: 19188–19194, 1988). To first assess the efficacy of permeabilization at different digitonin concentrations, 5–10 µg/ml of the DNA-binding fluorochrome propidium iodide (Jones, K. H. et al, "An improved method to determine cell viability by simultaneous staining with fluorescein diacetate-propidium iodide," *J. Histochem. Cytochem.*, 33: 77–79, 1985) was added to permeabilization buffer instead of labelled ATP. After incubation at 37° for 1–3 minutes, the buffer was removed and cells washed 3–4 times with PBS prior to fluorescence microscopy. Permeabilization was confirmed by the appearance of cells exhibiting nuclear fluorescence, since propidium iodide does not penetrate intact cells. Following $^{32}$P-labelling, cells were immediately harvested and lysates subject to SDS/8.5% polyacrylamide gel electrophoresis. Approximate molecular weights were determined using pre-stained protein markers (Amersham, Arlington Heights, Ill.). Dried gels were exposed to Kodak X-Omat AR film at −70° prior to development.

Miscellaneous Assays. Cell toxicity was determined using trypan blue exclusion as a marker for viable cells. Cells growing in 60 mm culture dishes were washed once with PBS, incubated at room temperature with 1 ml 0.4% trypan blue in normal saline (GIBCO, Rockville, Md.), washed twice with PBS, then placed on ice until cells were counted. Protein in cell lysates was determined using a commercial colorimetric assay (Bio-Rad Laboratories, Richmond, Calif.).

Results

Both TPA and Staurosporine Induce Maturation of Primary Keratinocytes In Vitro. Primary keratinocytes grown in 0.05 mM $Ca^{2+}$ medium exhibit a basal cell-like phenotype with well-defined intercellular spaces and a characteristic cobblestone-like appearance. FIG. 1 shows that staurosporine and TPA induce similar morphological changes in primary keratinocytes. Fresh medium containing 0.1% DMSO, 10 nM staurosporine, or 160 nM TPA was added to 5 day old primary keratinocyte cultures. Phase-contrast photomicrographs were taken at the indicated times after beginning treatment. Similar results were obtained in three additional experiments. Magnification was ×90. The addition of 10 nM staurosporine or 160 nM TPA results in a rapid alteration of cell morphology that is first detectable after 20 minutes. While both agents induce an elongated morphology by 3 hours, cells exposed to TPA are more extensively altered and frequently exhibit attenuated, dendrite-like processes (FIG. 1). After 24 hours, about 50% of the cells in TPA-treated cultures have rounded-up and detached from the substrate (FIG. 1): this is a characteristic response in keratinocytes that are pharmacologically induced to differentiate in medium with 0.05 mM $Ca^{2+}$ and does not reflect non-specific cytotoxicity. In contrast to TPA, nearly all cells in cultures exposed to staurosporine for 24 hours have detached from the substrate leaving behind a few small, bipolar cells (FIG. 1). Many remaining cells in TPA-treated cultures are immunoreactive for keratin 14 whereas none are positive in staurosporine-treated cultures (data not shown), indicating that staurosporine induces detachment of essentially all keratinocytes from the substrate. To determine if the morphological response to 10 nM staurosporine is caused by direct cytotoxicity, primary keratinocytes exposed to staurosporine were monitored by trypan blue exclusion. In DMSO controls and cultures treated with ≦10 nM staurosporine, <5% of the cells took up trypan blue. Not unexpectedly, substantial cell damage could be obtained at higher staurosporine doses, however, with 74% of cells trypan blue "positive" after a 7.5 hour exposure to 1 µM staurosporine (data not shown). These findings indicate that the morphological response to 10 nM staurosporine occurs in the absence of gross cytotoxicity.

Figure 2:
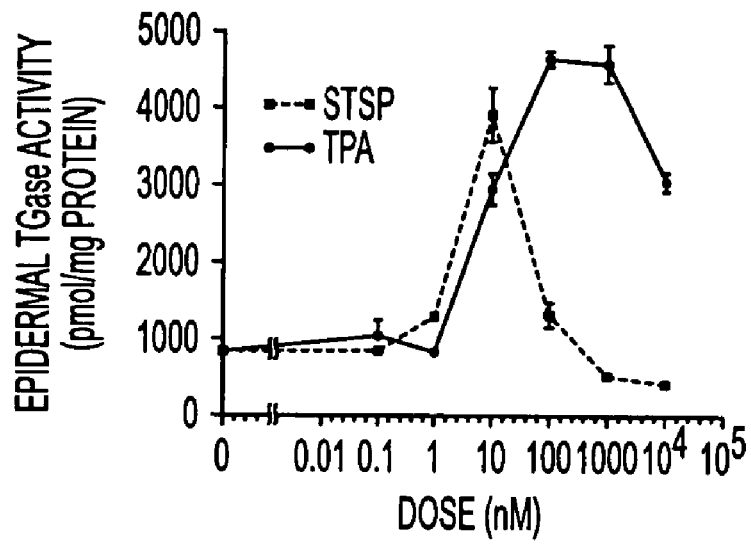
FIG. 2 is a graph showing epidermal transglutaminase activity versus dosage of TPA and staurosporine.

Epidermal transglutaminase activity is elevated in terminally differentiating keratinocytes both in vivo and in vitro. The addition of either staurosporine or TPA to 8 day old primary keratinocytes results in a dose-dependent induction of epidermal transglutaminase. FIG. 2 shows that both staurosporine and TPA activate epidermal transglutaminase in primary keratinocytes in a dosedependent manner. 8 day old cultures were harvested 9 hours after addition of 1.4 mM $Ca^{2+}$ medium containing staurosporine or TPA at the doses indicated. Control cultures (0 nM dose) were treated with 0.1% DMSO. Each point is the average of duplicate dishes with the range indicated by error bars. Staurosporine-induces a 4-fold increase in enzyme activity at 10 nMS TPA a 5-fold increase at 100 and 1000 nM (FIG. 2). The induction of transglutaminase activity by staurosporine is tightly restricted to a dose of 10 nM, while TPA-mediated activation occurs at doses ranging from 10 nM to 10 μM. The absence of transglutaminase induction at higher staurosporine doses is consistent with a toxic effect at concentrations of 100 nM or more while the 10 nM dose elicits a programmed response.

Figure 3:
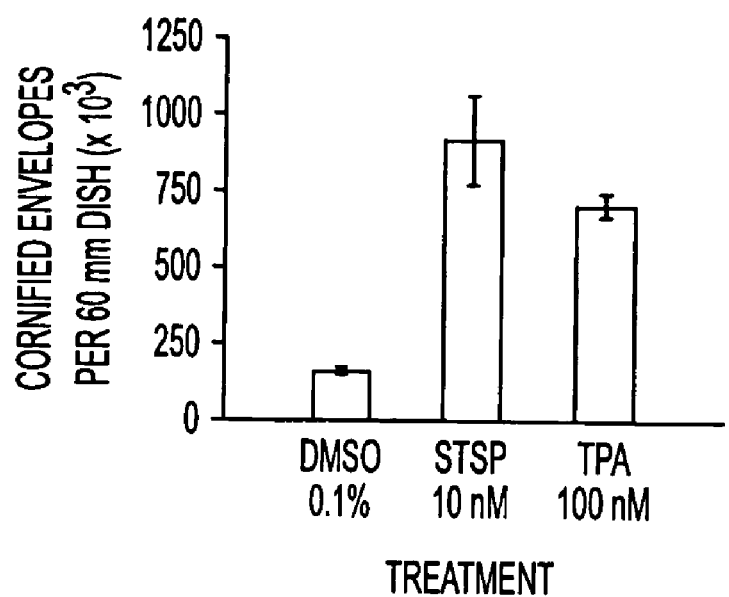
FIG. 3 is a graph showing inducement by staurosporine and TPA of cornified envelopes.

Activation of epidermal transglutaminase results in the assembly of rigid, detergent-insoluble cornified envelopes characteristic of terminally differentiated keratinocytes. To further evaluate the ability of staurosporine to induce keratinocyte maturation, cornified envelope formation was assessed in seven day old primary keratinocyte cultures exposed to medium with 0.1% DMSO, 10 nM staurosporine, or 160 nM TPA for 24 hours. Staurosporine induces a 5-fold increase in cornified envelopes relative to control cultures; TPA a 4-fold increase. FIG. 3 shows that both staurosporine and TPA induce cornified envelopes in primary keratinocytes. 7 day old primary keratinocyte cultures were exposed to 0.1% DMSO, 10 nM staurosporine, or 160 nM TPA for 24 hours. Floating and attached cell populations were harvested and cornified envelopes isolated. Data are mean values for three separate dishes±standard error of the mean from one experiment. Similar results were obtained in an additional experiment. The induction of both epidermal transglutaminase activity and cornified envelope formation by TPA and staurosporine indicates that both agents induce maturation in cultured primary mouse keratinocytes.

Figure 4:
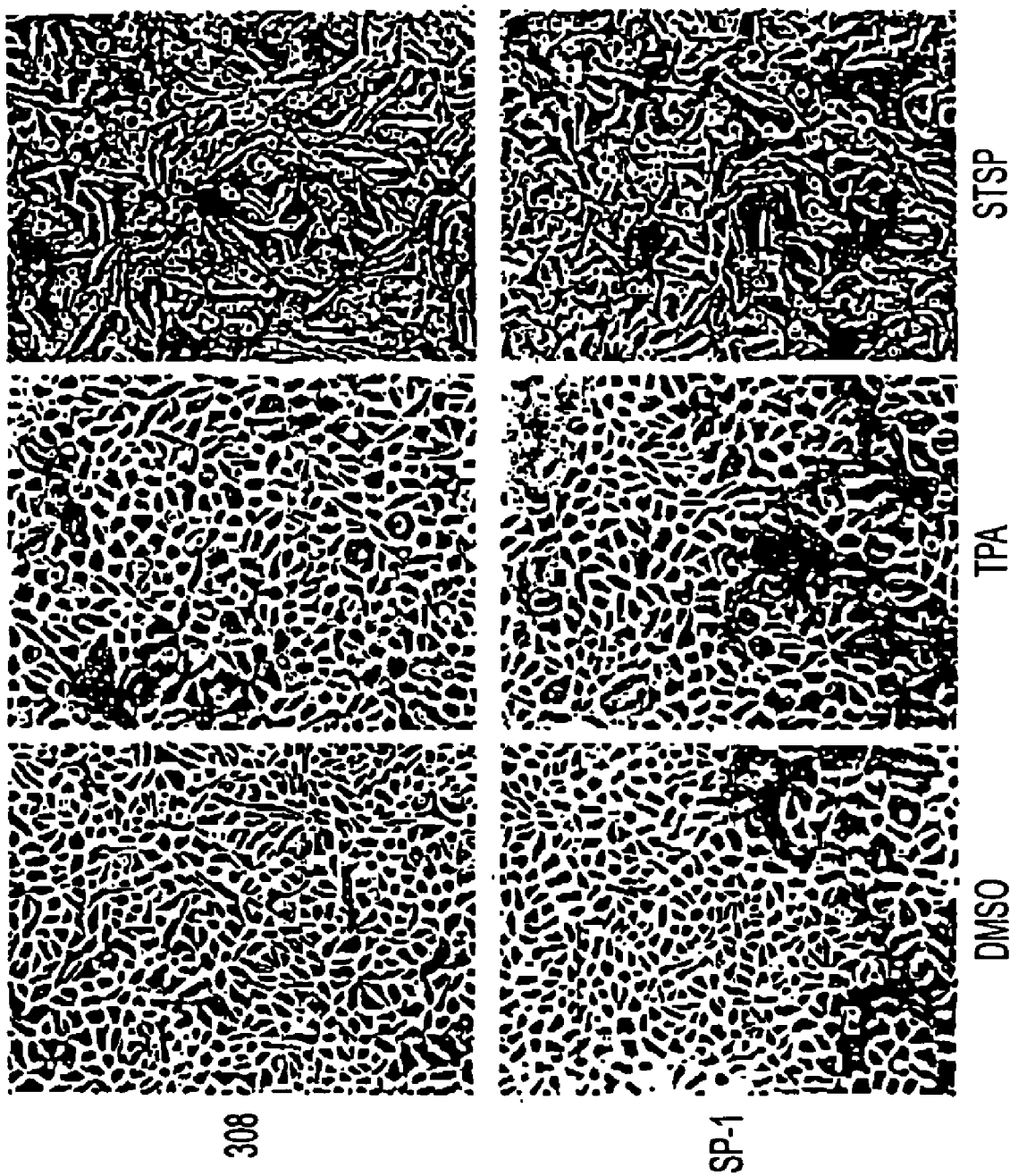
FIG. 4 shows phase-contrast photomicrographs (magnification×90) of staurosporine induced morphological differentiation in neoplastic keratinocyte cell lines.

Staurosporine But Not TPA Induces Maturation of Neoplastic Keratinocytes In Vitro. A basic defect of neoplastic keratinocytes is their inability to differentiate in response to either TPA or elevated extracellular $Ca^{2+}$, providing them with a potential growth advantage over normal cells in vivo. Since staurosporine induces differentiation in nearly the entire population of primary mouse keratinocytes exposed to this agent, we were interested in determining whether similar responses could be induced in neoplastic cells. The two cell lines selected for analysis, designated 308 and SP-1, cannot be induced to terminally differentiate in vitro and produce benign papillomas when grafted onto the backs of nude mice. After a 24 hour exposure to staurosporine, both 308 and SP-1 cells exhibit morphological changes similar to those seen in primary cells; in contrast, exposure to TPA does not appreciably alter the appearance of either cell line when compared with DMSO-treated controls. FIG. 4 shows that staurosporine induces morphological differentiation in neoplastic keratinocyte cell lines. 308 and SP-1 keratinocyte cell lines were exposed to 0.1% DMSO, 160 nM TPA, or 10 nM staurosporine for 24 hours. Note lack of response to TPA. Similar results were obtained in three additional experiments with each cell line. Magnification was x90. TPA was ineffective at inducing morphological differentiation at doses ranging from 1.6 nM to 16 uM (data not shown). Although the overall response pattern to staurosporine is the same in 308 and SP-1 cells as it is in primary keratinocytes the kinetics of this process is different: treatment for at least 48 hours is required for a maximal response in the cell lines compared with 24 hours for primary keratinocytes.

Figure 5:
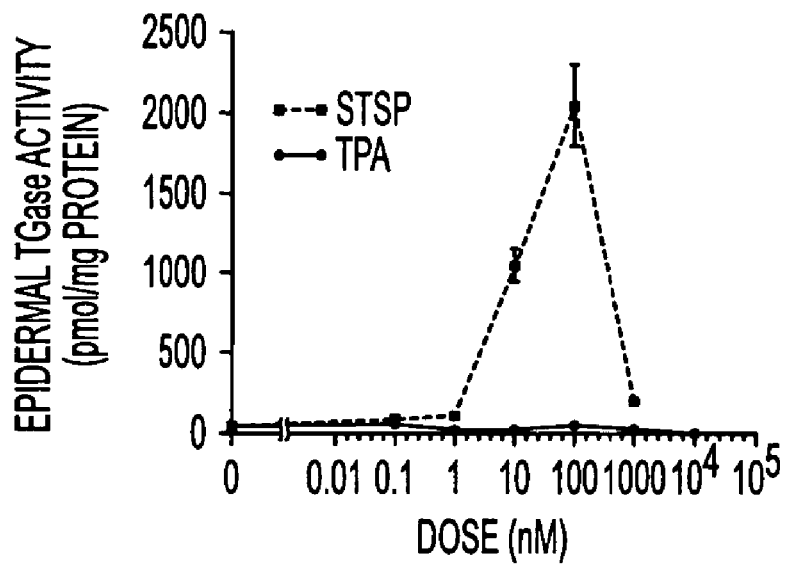
FIG. 5 is a graph showing epidermal transglutaminase activity versus dosage of TPA and staurosporine.

Epidermal transglutaminase was assayed to determine if staurosporine induces this differentiation marker in neoplastic keratinocytes as it does in primary cells. Exposure of SP-1 cells to staurosporine caused a dose-dependent increase in enzyme activity, with a maximum 50-fold induction at 100 nM. FIG. 5 shows that staurosporine induces epidermal transglutaminase in neoplastic keratinocytes in a dose-dependent manner. Epidermal transglutaminase activity was determined in cultures of 5 day old SP-1 cells exposed to the indicated concentrations of staurosporine or TPA for 24 hours. Control cultures (0 nM dose) were treated with 0.1% DMSO. Each data point is the average of duplicate dishes with the range indicated by error bars. An additional experiment using 10 nM staurosporine and 160 nM TPA yielded similar results. As with primary keratinocytes, higher doses were ineffective. In contrast to staurosporine, TPA had no detectable effect on epidermal transglutaminase activity at any dose ranging from 10 pM to 10 μM (FIG. 5).

Figure 6:
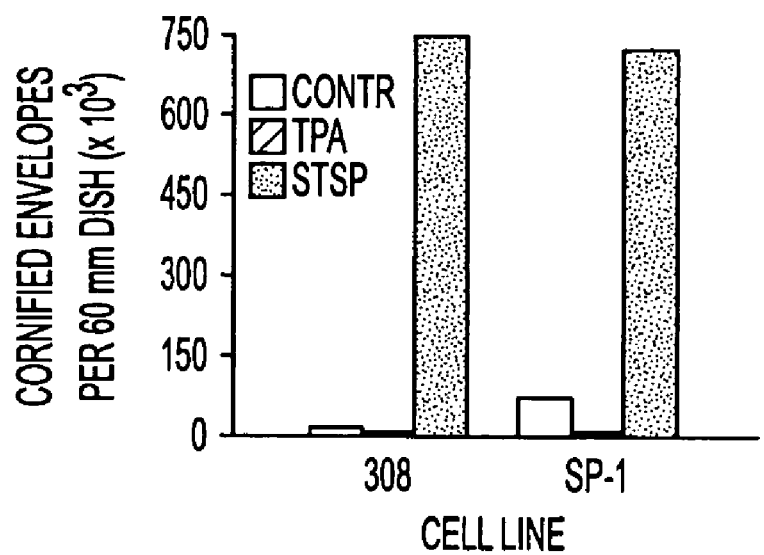
FIG. 6 is a graph showing inducement by staurosporine and TP of cornified envelopes.

Cornified envelope formation was also determined in cultures of staurosporine-treated neoplastic cells. Both neoplastic cell lines produced cornified envelopes when exposed to staurosporine, but not TPA. There was a 10-fold induction of cornified envelopes by staurosporine in SP-1 cells, a 60-fold induction in 308 cells. FIG. 6 shows that staurosporine induces cornified envelopes in neoplastic keratinocytes. 308 and SP-1 cells were exposed to 0.1% DMSO, 160 nM TPA, or 10 nM staurosporine in 1.4 mM $Ca^{2+}$ medium. After 3 days, cells were harvested and cornified envelopes isolated. Consistent with the results for epidermal transglutaminase activity, cornified envelope formation was not induced in TPA-treated cultures. These data indicate that staurosporine is a potent inducer of maturation in neoplastic keratinocyte cell lines that are entirely defective in their response to either TPA or $Ca^{2+}$ as inducers of differentiation.

Staurosporine Induces Certain Other Responses Characteristic of PKC Agonists. The ability of TPA and other phorbol esters to induce epidermal transglutaminase and cornified envelope formation in primary keratinocytes suggests that PKC activation is involved in this process. The induction of similar responses by staurosporine, a PKC inhibitor, was therefore unexpected. We have taken two approaches to further explore the potential involvement of PKC in staurosporine-mediated responses in keratinocytes: 1) cells rendered deficient in PKC were analyzed for their ability to respond to staurosporine: results from similar studies assessing effects of TPA have strongly implicated PKC in various responses to phorbol esters; 2) the ability of staurosporine to elicit several additional responses associated with PKC activation was examined: induction of ornithine decarboxylase, inhibition of $^{125}$I-EGF binding, expression of c-fos mRNA, and protein phosphorylation.

Staurosporine-mediated cornification is partially blocked in PKC-deficient primary keratinocytes. Bryostatin is an ultrapotent PKC modulator which interacts with the phorbol ester binding site of PKC and blocks many PKC-mediated responses in keratinocytes (Sako, T. et al, "Partial parallelism and partial blockade by bryostatin 1 of effects of phorbol ester tumor promoters on primary mouse epidermal cells,"

Figure 7:
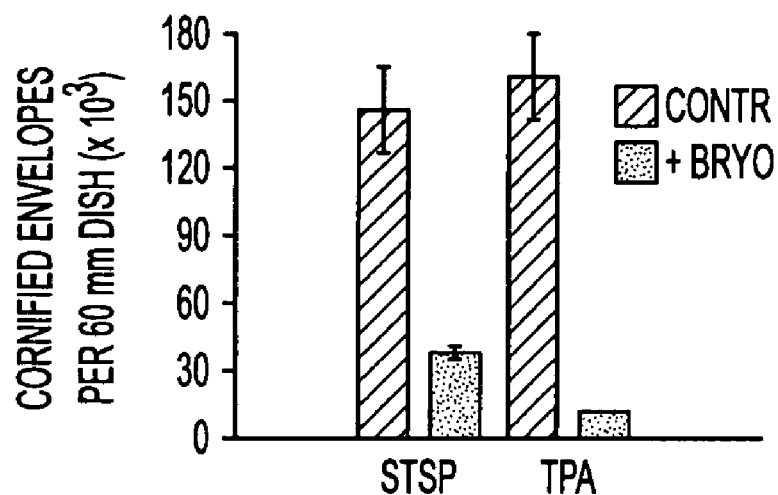
FIG. 7 is a graph showing down regulation of PKC which partially inhibits cornified envelope formation in primary keratinocytes exposed to staurosporine.

Cancer Res., 47: 5445–5450, 1987; Jetten, A. M. et al, "Action of phorbol esters, bryostatins, and retinoic acid on cholesterol sulfate synthesis: relation to the multistep process of differentiation in human epidermal keratinocytes," *J. Invest. Dermatol.*, 93: 108–115, 1989; and Gschwendt, M. et al, "An activator of protein kinase C, mimics as well as inhibits biological effects of the phorbol ester TPA in vivo and in vitro," *Carcinogenesis*, 9: 555–562, 1988) and other cell types (Dell'Aquila, M. L. et al, "Inhibition by bryostatin 1 of the phorbol ester-induced blockage of differentiation in hexamethylene bisacetamide-treated Friend erythroleukemia cells," *Cancer Res.*, 47: 6006–6009, 1987; Jetten, A. M. et al, "Effects of bryostatins and retinoic acid on phorbol ester- and diacylglycerol-induced squamous differentiation in human tracheobronchial epithelial cells," *Cancer Res.*, 49: 3990–3995, 1989: Kraft, A. S. et al, "An activator of the calcium phospholipid-dependent protein kinase, blocks phorbol ester-induced differentiation of human promyelocytic leukemia cells HL-60, " *Proc. Natl. Acad. Sci. USA*, 83: 1334–1338, 1986; and McBain, J. A. et al, "Bryostatin 1 antagonizes the terminal differentiating action of 12-0-tetradecanoylphorbol-13-acetate in a human colon cancer cell," *Carcinogenesis*, 9: 123–129, 1988). Staurosporine-mediated cornified envelope formation is blocked by bryostatin pre-treatment, as is that of TPA-treated cultures. FIG. 7 shows that down-regulation of PKC partially inhibits cornified envelope formation in primary keratinocytes exposed to staurosporine. 7 day old primary keratinocytes were cultured with or without 60 nM bryostatin for 15 hours. Fresh medium with 10 nM staurosporine or 160 nM TPA, ±bryostatin, was added for an additional 46 hours and cornified envelopes isolated. Each data bar is the average value from duplicate dishes with the range indicated by error bars. In an additional experiment, bryostatin pre-treatment reduced cornified envelope formation by 70% in both staurosporine and TPA-treated cultures. These data indicate the involvement of PKC in this response to staurosporine.

Figure 8:
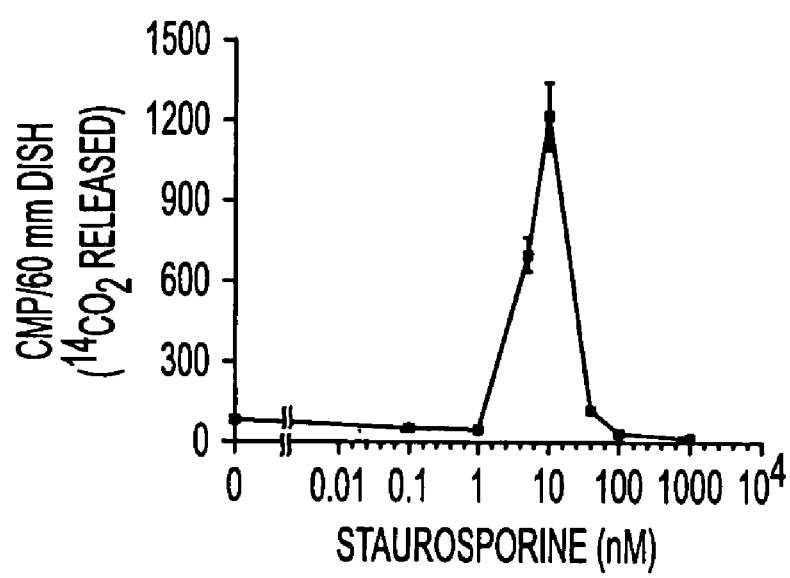
FIG. 8 is a graph showing inducement by staurosporine of ornithine decarboxylase activity in primary keratinocytes.

Both staurosporine and TPA induce ornithine decarboxylase activity in primary keratinocytes. Like TPA (Yuspa, S. H. et al, "Phorbol esters stimulate DNA synthesis and ornithine decarboxylase activity in mouse epidermal cell cultures," *Nature*, 262: 402–404, 1976), exposure to staurosporine results in induction of ornithine decarboxylase activity in cultured primary mouse keratinocytes. FIG. 8 shows that staurosporine induces ornithine decarboxylase activity in primary keratinocytes. Primary mouse keratinocyte cultures exposed to the indicated concentrations of staurosporine for 5 hours were harvested for analysis of ornithine decarboxylase activity. Each point is the mean for four dishes±standard error of the mean from one experiment. Similar results were obtained in an additional experiment. As with staurosporine-mediated induction of transglutaminase, this response is restricted to a narrow dose range between 5 and 10 nM.

Figure 9:
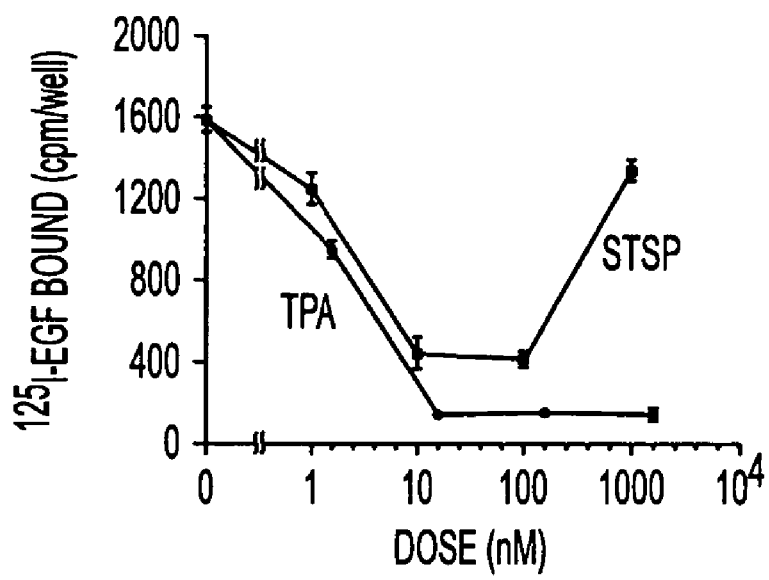
FIG. 9 is a graph showing inhibition of $^{125}$I-EGF by staurosporine and TPA.

Both staurosporine and TPA inhibit $^{125}$I-EGF binding in primary keratinocytes. Exposure of a variety of cultured cell types to TPA results in inhibition of EGF binding which is attributed to PKC-mediated phosphorylation of the EGF receptor (Diamond, L., "Tumor promoters and cell transformation," In: D. Grunberger and S. P. Goff. (eds.), *Mechanisms of Cellular Transformation by Carcinogenic Agents*, pp. 73–133, New York: Pergamon Press. 1987). TPA and staurosporine rapidly inhibit binding of $^{125}$I-EGF to primary keratinocytes: exposure to 160 nM TPA causes a 94% reduction, 10 nM staurosporine a 72% reduction relative to controls. FIG. 9 shows that staurosporine and TPA inhibit $^{125}$I-EGF binding in a dose-dependent manner. 7 day old primary keratinocytes were treated with different doses of staurosporine or TPA for 2.5 hours. Each data point represents the average $^{125}$I-EGF binding±standard error of the mean for three dishes. As noted above for other parameters, the lack of response to 1 µM staurosporine may reflect cytotoxicity at this high dose.

Figure 10:
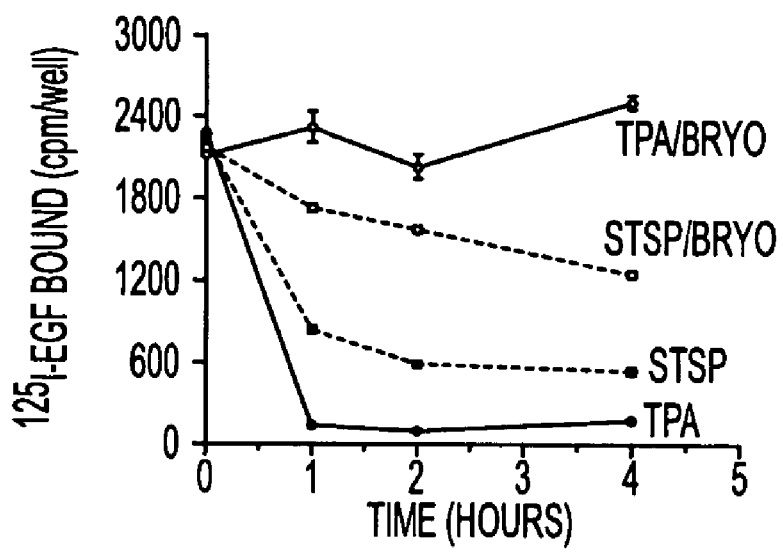
FIG. 10 is a graph showing that down-regulation of PKC partially inhibits staurosporine-mediated inhibition of $^{125}$I-EGF binding.

To assess the role of PKC in the inhibition of $^{125}$I-EGF binding in primary keratinocytes, PKC-deficient cells were generated by exposing cultures to 60 nM bryostatin for 1 day. Both TPA- and staurosporine-mediated inhibition of $^{125}$I-EGF binding was inhibited over a 4 hour period: bryostatin pre-treatment completely blocked the response to TPA, while it blocked the response to staurosporine by an average 50%. FIG. 10 shows that down-regulation of PKC partially inhibits staurosporine-mediated inhibition of $^{125}$I-EGF binding. 6 day old primary keratinocytes were cultured with or without 60 nM bryostatin for 1 day, followed by the addition of staurosporine or TPA±bryostatin as indicated. Cultures were harvested for analysis of $^{125}$I-EGF binding 1, 2, and 4 hours later. Each point is the mean of trilpicate dishes±standard error of the mean. These findings suggest that PKC is involved in the inhibition of $^{125}$I-EGF binding in response to both TPA and staurosporine.

Figure 11:
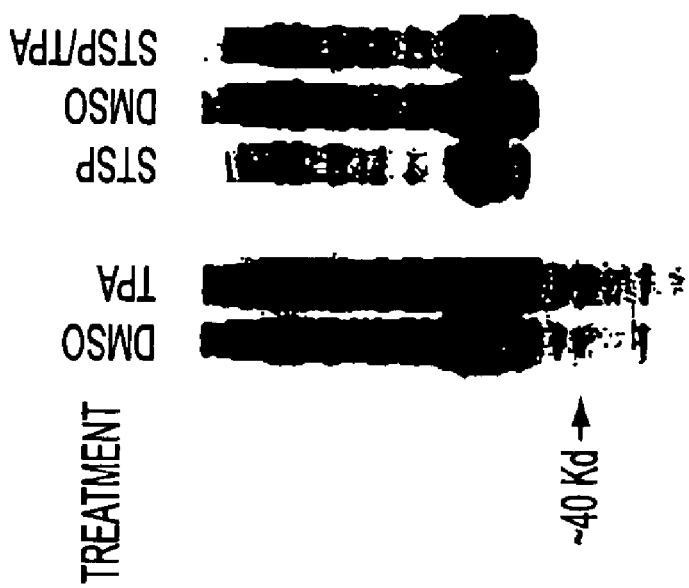
FIG. 11 is a blot analysis showing inducement of c-fos mRNA by staurosporine and TPA.

Both TPA and staurosporine induce c-fos mRNA. TPA rapidly induces transcription of the protooncogene c-fos, which is a useful marker for PKC activation in a variety of cells (Curran, T., "The fos oncogene," In: E. P. Reddy, A. M. Skalka and T. Curran (eds.), *The Oncogene Handbook*, pp. 307–325, Amsterdam: Elsevier. 1988). In primary mouse keratinocytes, TPA causes a sustained elevation of steady-state c-fos mRNA during an 8 hour treatment with maximum expression at 6 hours. FIG. 11 shows that both TPA and staurosporine induce c-fos MRNA. 6–7 day old primary keratinocytes were grown in complete medium with 0.5% serum for 1 day. Reagents were added directly to culture medium and cells harvested at the indicated times for RNA isolation. Staurosporine (STSP) was added just before TPA when these agents were combined. Each lane contains 20 µg of total RNA; staining with ethidium bromide or hybridization to a GAPDH control probe confirmed uniformity of loading in all lanes. c-fos MRNA was identified using a 1.2 kb $^{32}$P-labelled murine c-fos DNA probe. The results illustrated were obtained using RNA from two separate experiments. In cultures exposed to staurosporine, c-fos is also induced but with different kinetics and to a lesser extent than TPA. The greatest induction is at 8 hours of staurosporine treatment with very low levels at 1 and 6 hours (FIG. 11). Combined exposure to both staurosporine and TPA induces higher expression of c-fos MRNA than TPA alone (FIG. 11). These results again indicate both the inability of staurosporine to block certain TPA-mediated responses and the mimicry of TPA which it can induce.

Figure 12:
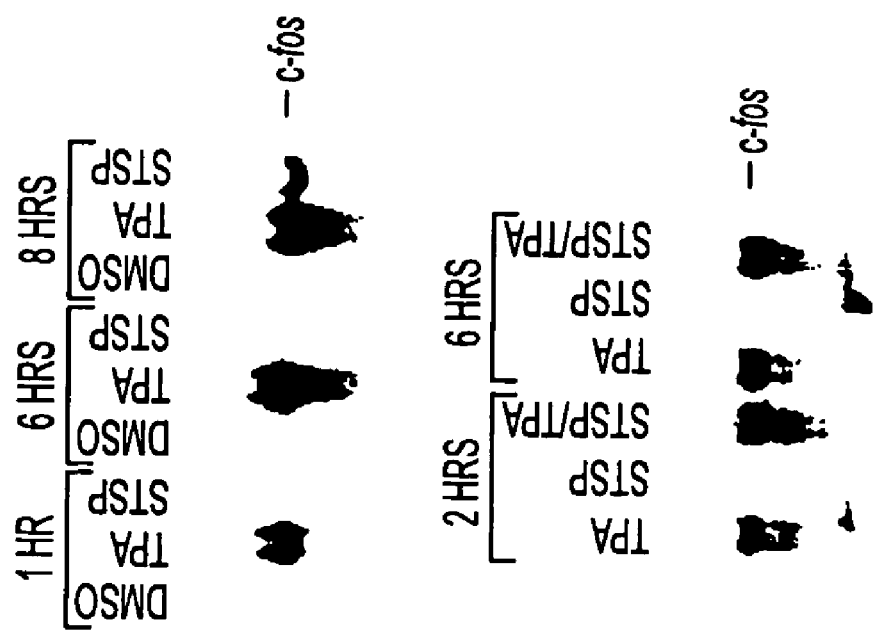
FIG. 12 is a blot analysis showing that TPA but not staurosporine induces phosphorylation of a 40 kD protein.

TPA but not staurosporine induces phosphorylation of an ~40 kD protein in digitonin-permeabilized keratinocytes. The data presented thus far are consistent with the hypothesis that staurosporine acts as a PKC agonist in keratinocytes based on the findings that 1) the pattern of multiple responses to staurosporine is remarkably similar to that seen with TPA exposure, and 2) some of these responses are blocked, at least partially, in cells rendered deficient in PKC. To directly assess the ability of staurosporine to affect kinase activity, digitonin-permeabilized primary keratinocytes were incubated with $\gamma^{32}$P-ATP and labelled phosphoproteins analyzed by SDS/PAGE and autoradiography. Exposure of primary keratinocytes to 160 nM TPA resulted in enhanced phosphorylation of a band migrating at about 40 kD (pp40). FIG. 12 shows that TPA but not staurosporine induces phosphorylation of a 40 kD protein. 5 day old primary keratinocyte cultures were exposed for 3 minutes to permeabilization buffer (30 μM digitonin, 10 μM $\gamma^{32}$P-ATP [specific activity 1 Ci/mmol]) containing 0.1 or 0.2% DMSO, 160 nM TPA, 10 nM staurosporine (STSP), or both TPA and staurosporine. Cells were harvested immediately and proteins separated by SDS/PAGE. Dried gels were exposed to Kodak X-Omat AR film at −70° for 12–24 hours prior to development. This band was not detected in cultures exposed to staurosporine, which exhibited a reduction in overall protein phosphorylation relative to control cultures (FIG. 12). Additional doses of staurosporine ranging from 0.1 to 5 nM were also ineffective at inducing phosphorylation of pp 40(data not shown). Co-exposure to TPA and staurosporine blocked the TPA-mediated phosphorylation of pp 40(FIG. 12). These data indicate that under the conditions used for this experiment, staurosporine not only fails to phosphorylate a putative PKC substrate but also inhibits TPA-mediated phosphorylation of this protein.

EXAMPLES

Staurosporine is shown to induce terminal differentiation in cultured mouse papilloma cell lines 308 and SP-1, which are resistant to this induction by phorbol esters and $Ca^{2+}$. For grafting, BALB/c-derived nude mice, approximately two months-old, were used as hosts. Animals were anesthetized with Nembutal and sterile surgical technique was used. $0.5 \times 10^6$ SP-1 or 308 cells were grafted along with $6-8 \times 10^6$ primary SENCAR mouse dermal fibroblasts. Cell pellets were applied within a silicone chamber to a graft bed as described in Strickland et al, *Cancer Res.*, 48: 165–169 (1988). Cells were removed from culture dishes by treatment with 0.25% trypsin-0.01% EDTA for approximately 10 min. at 36° and washed with medium. Suspensions of papilloma cells and primary dermal fibroblasts were centrifuged 5 min. at 1000 rpm, the medium aspirated, and the cell pellet applied to the graft bed using a sterile plastic transfer pipet. Graft tumors were measured weekly, using calipers, starting three weeks after grafting and for at least 5 additional weeks thereafter. As an approximate tumor volume, the height was multiplied by the smallest and largest lateral measurements. Data are expressed as means i standard error of the mean of approximate tumor volume in $mm^3$. Grafting of 308 and SP-1 cells to athymic nude mouse hosts produces squamous papillomas, which are benign precursors of malignant squamous cell carcinomas. Growth of these papillomas is inhibited in a dose-dependent manner by topical treatment with staurosporine, beginning two weeks after grafting. Twice-weekly exposures to 0.025 nmole staurosporine in acetone were optimal for inhibition. Higher doses (6.25 nmoles/treatment) appear to stimulate papilloma growth. A single low-dose treatment two weeks after grafting also reduced tumor formation, indicating the inhibition was permanent.

Example 1

Topical Treatment With Staurosporine Inhibits Tumor Formation From Grafted SP-1 Mouse Papilloma Cells Approximate tumor volumes are compared during an eight week period for two groups: an acetone (solvent) control and a staurosporine-treated group. Five mice in each group were grafted Feb. 28, 1990 with $0.5 \times 10^6$ SP-1 cells+ $6 \times 10^6$ primary SENCAR mouse dermal fibroblasts.

SP-1 cells are a benign tumor line derived from squamous papillomas produced on SENCAR mice by initiation with 7,12-dimethylbenz[a]anthracene (DMBA) and promotion with 12-0-tetradecanoylphorbol-13-acetate (TPA). SP-1 cells form benign epidermal tumors (squamous papillomas) when grafted to athymic nude mouse hosts in this manner.

Figure 13:
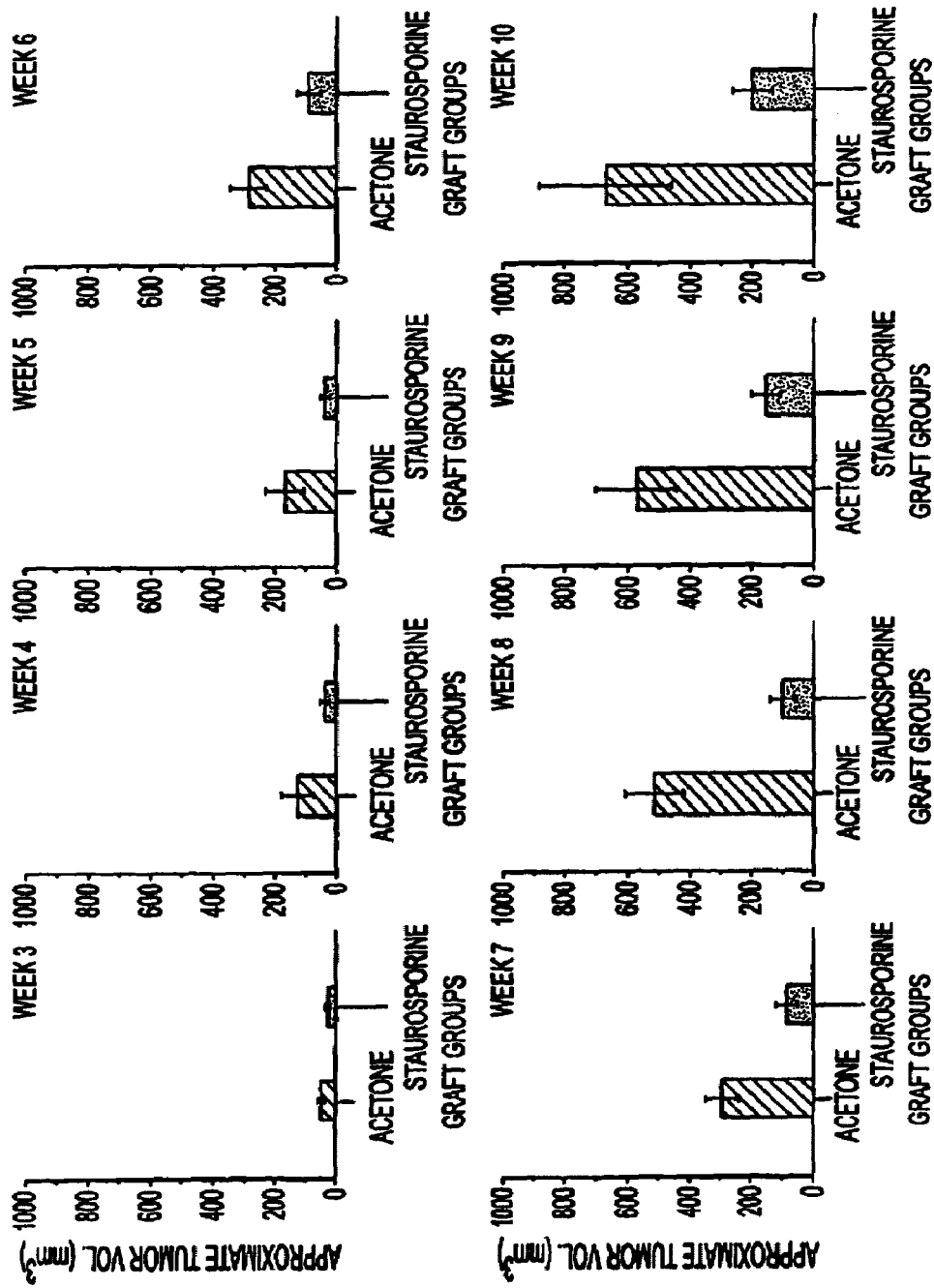
FIGS. 13–18 are graphs of the results of Examples 1–6, respectively.

Graft sites were treated once a week with 2.5 nmole staurosporine in 25 μl acetone or with 25 μl acetone, beginning two weeks after grafting and continuing until the termination of the experiment. Tumor measurements were begun three weeks after grafting and continued for eight weeks. Inhibition of tumor size by staurosporine was clear as early as four weeks after grafting (two weeks after beginning staurosporine treatment) as shown by the results in FIG. 13.

Example 2

Inhibition of Tumor Formation From Grafted SP-1 Mouse Papilloma Cells by Staurosporine Approximate tumor volumes are compared during an eight week period for six groups: an acetone (solvent) control and six doses of staurosporine. Ten mice in each group were grafted Mar. 22, 1990 with $0.5 \times 10^6$ SP-1 cells+ $6 \times 10^6$ primary SENCAR mouse dermal fibroblasts.

SP-1 cells are a benign tumor line derived from squamous papillomas produced on SENCAR mice by initiation with 7,12-dimethylbenz[a]anthracene (DMBA) and promotion with 12-0-tetradecanoylphorbol-13-acetate (TPA). SP-1 cells form benign epidermal tumors (squamous papillomas) when grafted to athymic nude mouse hosts in this manner.

Figure 14:
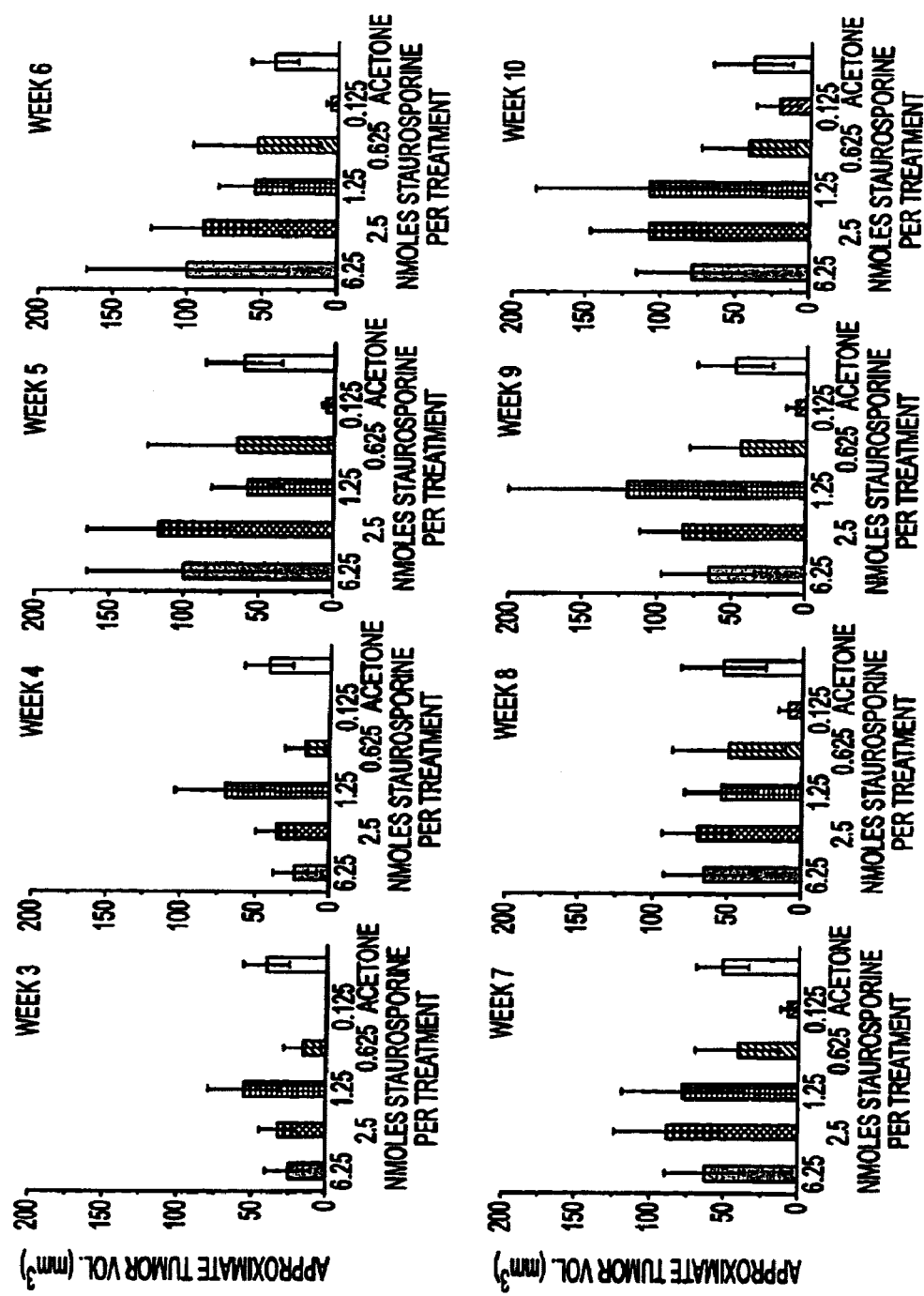

Graft sites were treated twice per week with the indicated amount of staurosporine in 25 μl acetone or with 25 μl acetone, beginning two weeks after grafting and continuing until the termination of the experiment. Tumor measurements were begun three weeks after grafting and continued for eight weeks. The optimum dose of 0.125 nmole staurosporine was apparent from the first tumor measurements (Week 3) as shown in the FIG. 14 results. This was the first suggestion that a single dose given early enough might be highly effective. Since the lowest dose tested, 0.125 nmole per treatment, was most effective, it was necessary to test lower doses to find the optimum dosage.

Example 3

Inhibition of Tumor Formation From Grafted SP-1 Mouse Papilloma Cells by Staurosporine Approximate tumor volumes are compared during an eight week period for six groups: an acetone (solvent) control and six doses of staurosporine. Ten mice in each group were grafted May 17, 1990 with $0.5 \times 10^6$ SP-1 cells+ $6 \times 10^6$ primary SENCAR mouse dermal fibroblasts. This is a repeat of Example 2 except that the highest (6.25 nmole) and third highest (1.25 nmole) doses were eliminated and two additional doses (0.025 nmole & 0.00625 nmole), lower than the previous lowest dose (0.125 nmole) used in Example 3, were added.

SP-1 cells are a benign tumor line derived from squamous papillomas produced on SENCAR mice by initiation with 7,12-dimethylbenz[a]anthracene (DMBA) and promotion with 12-0-tetradecanoylphorbol-13-acetate (TPA). SP-1 cells form benign epidermal tumors (squamous papillomas) when grafted to athymic nude mouse hosts in this manner.

Figure 15:
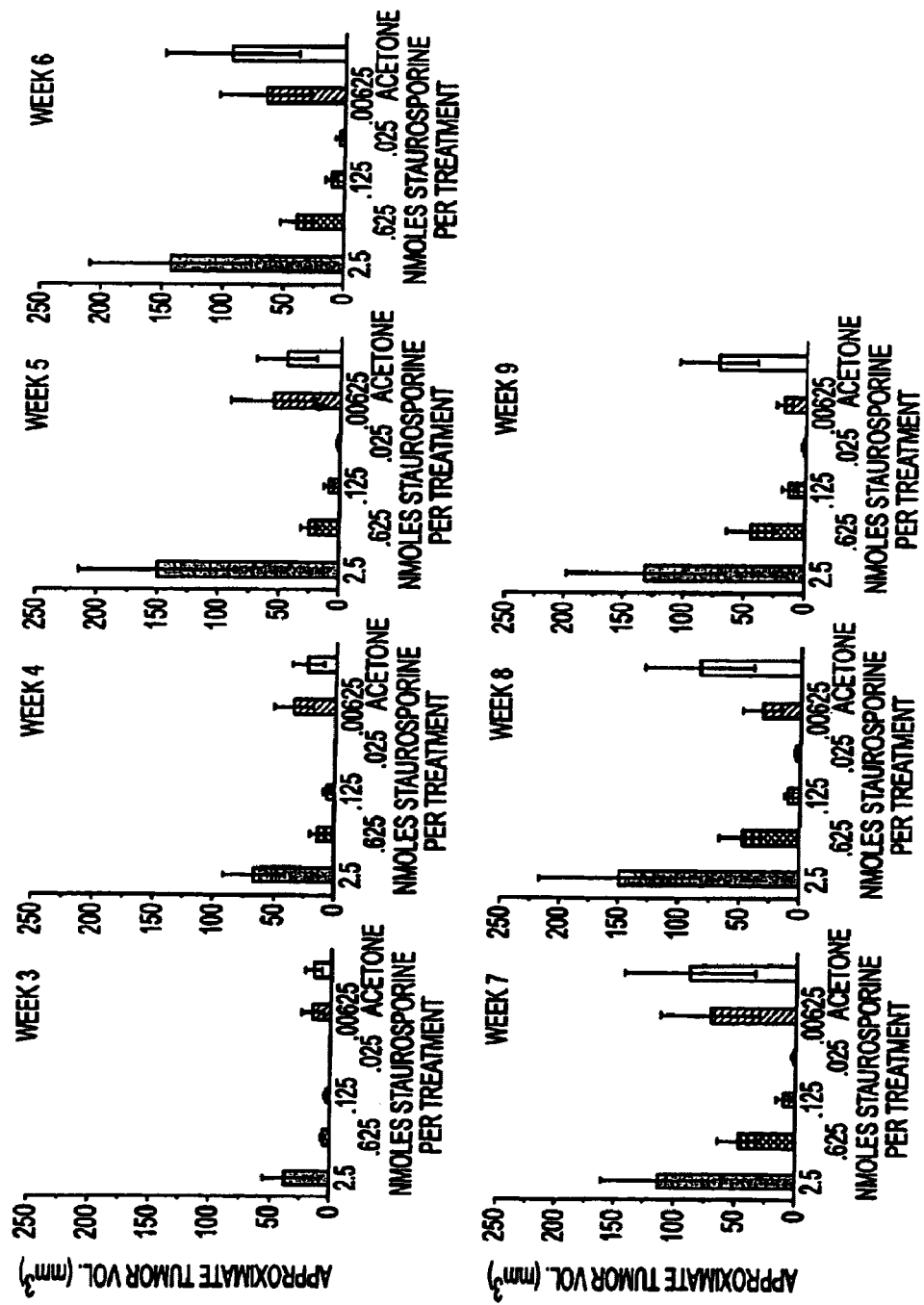

Graft sites were treated twice per week with the indicated amount of staurosporine in 25 μl acetone or with 25 μl acetone, beginning two weeks after grafting and continuing until the termination of the experiment. Tumor measurements were begun three weeks after grafting and continued for seven weeks. The optimum dose of 0.025 nmole staurosporine was apparent from the first tumor measurements (Week 3) as shown in the FIG. 15 results. The doses effective in Example 3 (0.625 & 0.125 nmole) were also effective in this example, and the effective doses were apparent from the first week of tumor measurements.

Example 4

Inhibition of Tumor Formation From Grafted 308 Mouse Papilloma Cells by Staurosporine Approximate tumor volumes are compared during an eight week period for six groups: an acetone (solvent) control and six doses of staurosporine. Ten mice in each group were grafted Aug. 8, 1990 with $0.5\times10^6$ 308 cells+$6\times10^6$ primary SENCAR mouse dermal fibroblasts. This is a repeat of Example 3 except that 308 cells were used in place of SP-1 cells to determine whether the staurosporine inhibitory effect was limited to SP-1 cells or was more generally effective with murine benign epidermal cell tumor lines.

308 cells are a benign tumor line derived from skin of BALB/c mice treated with an initiating dose of 7,12-dimethylbenz[a]anthracene (DMBA). Initiated cells were selected in culture by resistance to induction of terminal differentiation by increased $Ca^{2+}$ concentration in the medium. This resistance to $Ca^{2+}$-induced terminal differentiation is a property of initiated cells, which are the precursors of benign squamous papillomas resulting from tumor promotion. Like SP-1 cells, 308 cells form squamous papillomas when grafted to athymic nude mouse hosts.

Figure 16:
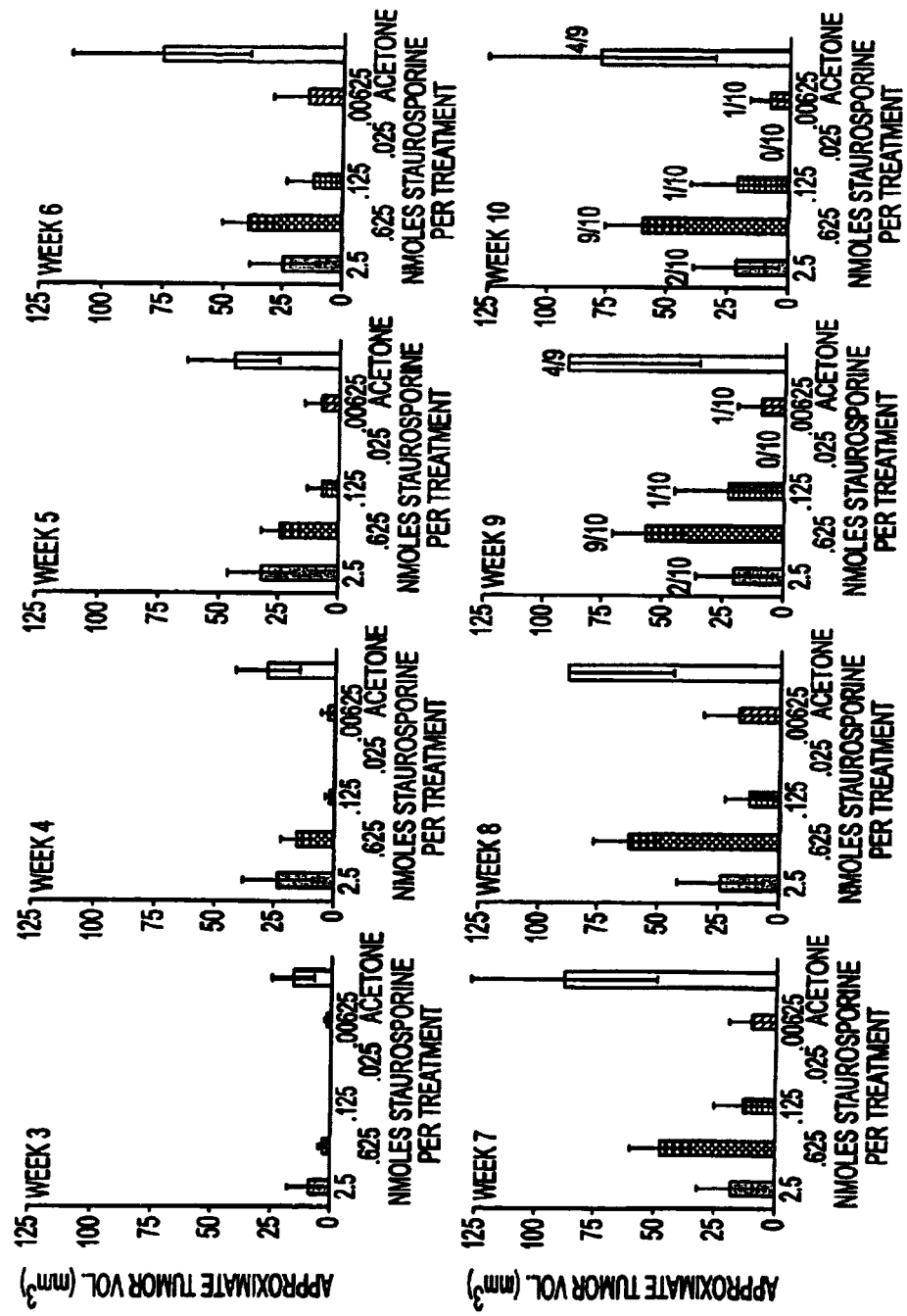

Graft sites were treated twice per week with the indicated amount of staurosporine in 25 μl acetone or with 25 μl acetone, beginning two weeks after grafting and continuing until the termination of the experiment. Tumor measurements were begun three weeks after grafting and continued for eight weeks. The optimum dose of 0.025 nmole staurosporine was apparent from the first tumor measurements (Week 3) and was the same optimum dose as that seen for SP-1 cells in Example 4 as shown in the FIG. 16 results. The 0.625 & 0.125 nmole doses were also effective in this example, as they were with SP-1 cells.

Example 5

Single treatment of grafted SP-1 mouse papilloma cells with staurosporine two weeks after grafting is effective in inhibiting tumor formation throughout the following eight weeks.

Approximate tumor volumes are compared during an eight week period for six groups: an acetone (solvent) control and six doses of staurosporine. Ten mice in each group were grafted Sep. 13, 1990 with $0.5\times10^6$ SP-1 cells+$6\times10^6$ primary SENCAR mouse dermal fibroblasts. This is a repeat of Example 3 with the same staurosporine doses except that only a single topical treatment with staurosporine in 25 μl acetone or with 25 μl acetone was done.

SP-1 cells are a benign tumor line derived from squamous papillomas produced on SENCAR mice by initiation with 7,12-dimethylbenz[a]anthracene (DMBA) and promotion with 12-0-tetradecanoylphorbol-13-acetate (TPA). SP-1 cells form benign epidermal tumors (squamous papillomas) when grafted to athymic nude mouse hosts in this manner.

Figure 17:
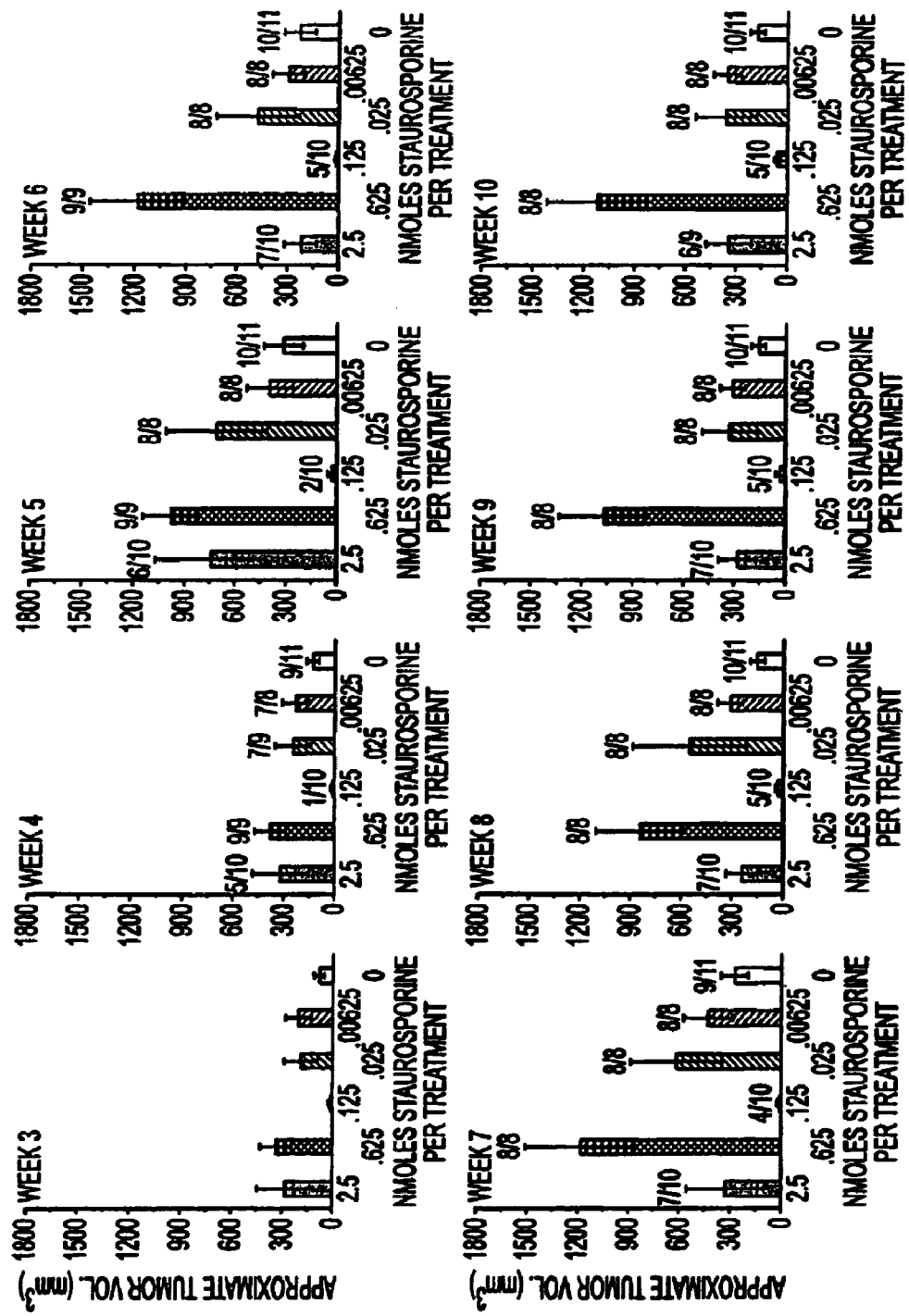

Graft sites were treated once, at two weeks after grafting, with the indicated amount of staurosporine in 25 μl acetone or with 25 μl acetone. Tumor measurements were begun three weeks after grafting and continued for eight weeks. The most inhibitory dose, 0.125 nmole, was effective in all the previous experiments, with both SP-1 and 308 cells. Tumor growth seemed to be faster in this example than in previous ones as is seen by the results shown in FIG. 17. The possibly increased number of tumor cells present at the time of treatment may explain what appears to be a shift to a higher optimum dose that seen with repeated treatments.

Example 6

Single treatment of grafted 308 mouse papilloma cells with staurosporine two weeks after grafting is effective in inhibiting tumor formation throughout the following eight weeks.

Approximate tumor volumes are compared during an eight week period for six groups: an acetone (solvent) control and six doses of staurosporine. Ten mice in each group were grafted Sep. 19, 1990 with $0.5\times10^6$ 308 cells+$6\times10^6$ primary SENCAR mouse dermal fibroblasts. This is a repeat of Example 4 with the same staurosporine doses except that only a single topical treatment with staurosporine in 25 μl acetone or with 25 μl acetone was done.

308 cells are a benign tumor line derived from skin of BALB/c mice treated with an initiating dose of 7,12-dimethylbenz[a]anthracene (DMBA). Initiated cells were selected in culture by resistance to induction of terminal differentiation by increased $Ca^{2+}$ concentration in the medium. This resistance to $Ca^{2+}$-induced terminal differentiation is a property of initiated cells, which are the precursors of benign squamous papillomas resulting from tumor promotion. Like SP-1 cells, 308 cells form squamous papillomas when grafted to athymic nude mouse hosts.

Figure 18:
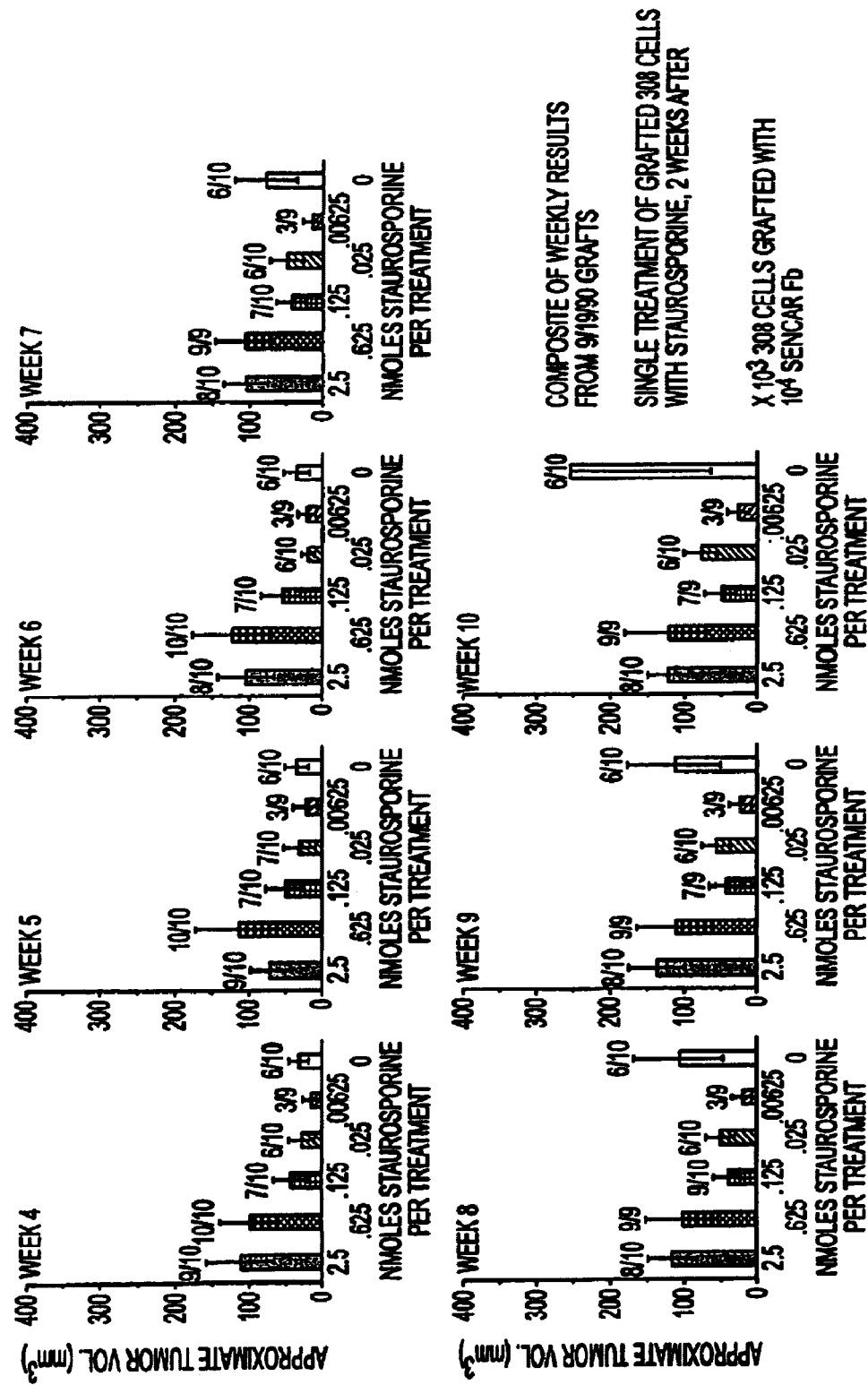

Graft sites were treated once, at two weeks after grafting, with the indicated amount of staurosporine in 25 μl acetone or with 25 μl acetone. Tumor measurements were begun three weeks after grafting and continued for eight weeks. The inhibitory doses, 0.125, 0.025, and 0.00625 nmole, were effective in previous experiments, with both SP-1 and 308 cells. The results are shown in FIG. 18.

Results of the grafting studies indicate that treatment with low doses (0.025 nmole) of staurosporine is effective in inhibiting tumor formation from at least two types of grafted benign skin tumor cells. Topical treatment is an effective mode of delivery of the drug, and acetone is an effective solvent. A single treatment with the drug, if given sufficiently early after the lesion develops, may be as effective as repeated treatments.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for treating epithelial cancers selected from keratoacanthoma, actinic kertosis, basal cell carcinoma, squamous cell carcinoma, Bowen's disease and verrucae which comprises administering topically to an affected area of the skin of a patient in need of such treatment a composition which comprises a pharmaceutically acceptable excipient in combination with an effective amount of staurosporine compound to cause terminal differentiation in cells of the epithelial cancer thereby ridding the patient of the cancer cells in the treated area.

2. The method of claim 1, wherein said effective amount is between about 1.25 and about 0.00625 nmol per $cm^2$.

3. The method of claim 1, wherein said effective amount is between about 0.625 and about 0.00625 nmol per $cm^2$.

4. The method of claim 1, wherein said effective amount is less than or equal to about 1.25 nmol per $cm^2$.

5. The method of claim 1, wherein said effective amount is less than or equal to about 0.125 nmol per $cm^2$.

6. The method of claim 1, wherein said effective amount is about 0.025 nmol per $cm^2$.

7. The method of claim 1, wherein said topical administration is a single application.

8. The method of claim 1, wherein said topical administration is a series of administrations.

* * * * *